US007623969B2

(12) United States Patent
Hood et al.

(10) Patent No.: US 7,623,969 B2
(45) Date of Patent: Nov. 24, 2009

(54) GENE DISCOVERY FOR THE SYSTEM ASSIGNMENT OF GENE FUNCTION

(75) Inventors: Leroy E. Hood, Seattle, WA (US); Andrew F. Siegel, Shoreline, WA (US); Trey E. Ideker, Cambridge, MA (US)

(73) Assignee: The Institute for Systems Biology, Seattle, WA (US)

( * ) Notice: Subject to any disclaimer, the term of this patent is extended or adjusted under 35 U.S.C. 154(b) by 0 days.

(21) Appl. No.: 10/062,299

(22) Filed: Jan. 31, 2002

(65) Prior Publication Data

US 2003/0143520 A1 Jul. 31, 2003

(51) Int. Cl.
*G01N 33/48* (2006.01)
(52) U.S. Cl. .............................. 702/19; 702/20; 703/11; 707/102; 435/6; 435/7.1
(58) Field of Classification Search ................... 702/19; 435/6; 706/48
See application file for complete search history.

(56) References Cited

U.S. PATENT DOCUMENTS

| 5,814,445 | A | 9/1998 | Belyavsky et al. | 435/6 |
|---|---|---|---|---|
| 5,980,096 | A | 11/1999 | Thalhammer-Reyero | 364/578 |
| 6,132,969 | A * | 10/2000 | Stoughton et al. | 435/6 |
| 6,188,988 | B1 | 2/2001 | Barry et al. | 705/3 |
| 6,194,217 | B1 | 2/2001 | Matson | 436/63 |
| 6,203,987 | B1 | 3/2001 | Friend et al. | 435/6 |
| 6,287,765 | B1 | 9/2001 | Cubicciotti | 435/6 |
| 7,343,247 | B2 | 3/2008 | Hood et al. | |
| 2001/0034580 | A1 | 10/2001 | Skolnick et al. | 702/19 |
| 2001/0044699 | A1 | 11/2001 | Ewing et al. | 702/19 |

FOREIGN PATENT DOCUMENTS

| WO | WO 99/11822 | 3/1999 |
|---|---|---|
| WO | WO 99/57130 | 11/1999 |
| WO | WO 00/11208 | 3/2000 |
| WO | WO 00/45322 | 8/2000 |

OTHER PUBLICATIONS

Aebersold et al., "Equipping scientists for the new biology," *Nature Biotechnology* 18:359 (2000).
Alper J., "Weighing DNA for fast genetic diagnosis," *Science* 279:2044-2045 (1998).
Anderson, *An Introduction to Multivariate Statistical Analysis*, second ed., chapter 6, pp. 195-243 Wiley, New York (1984).

(Continued)

*Primary Examiner*—Carolyn L. Smith
(74) *Attorney, Agent, or Firm*—McDermott Will & Emery LLP

(57) ABSTRACT

The invention provides a method for assigning a cellular function to a component of a biochemical system. The method involves (a) determining a multidimensional shape space for one or more components of a biochemical system in a reference state; (b) perturbing a component within said biochemical system; (c) determining a perturbed multidimensional shape space for one or more components of a pathway in said perturbed biochemical system, and (d) identifying a multidimensional coordinate point corresponding to a component of said perturbed pathway altered between reference and perturbed multidimensional shape spaces, said identified component being assigned a cellular function of said perturbed pathway.

14 Claims, 2 Drawing Sheets

OTHER PUBLICATIONS

Burton and Harding, "Hydrophobic charge induction chromatography: salt independent protein adsorption and facile elution with aqueous buffers," *J. Chromatography* 814:71-81 (1998).

Cheng and Church, "Biclustering of Expression Data," *Proc. Int. Conf. Intell. Syst. Mol. Biol.* 8:93-103 (2000).

Eichler et al., "Peptide, peptidomimetic, and organic synthetic combinatorial libraries," *Med. Res. Rev.* 15:481-496 (1995).

Eisenberg et al., "Protein function in the post-genomic era," *Nature* 405:823-826 (2000).

Ellington and Szostak, "In vitro selection of RNA molecules that bind specific ligands," *Nature* 346:818-822 (1990).

Emili and Cagney, "Large-scale functional analysis using peptide or protein arrays," *Nature Biotech.* 18:393-397 (2000).

Fellenberg et al., "Integrative Analysis of Protein Interaction Data," *Proc. Int. Cont. Intell. Syst. Mol. Biol.* 8:152-161 (2000).

Famulok M., "Oligonucleotide aptamers that recognize small molecules," *Current Opinion in Structural Biology* 9:324-329 (1999).

Famulok and Mayer, "Aptamers as tools in molecular biology and immunolgoy," *Curr. Top. Microbiol. Immunol.* 243:123-136 (1999).

Fang et al., "Designing a novel molecular beacon for surface-immobilized DNA hybridization studies," *J. Am. Chem. Soc.* 121:2921-2922 (1999).

Fang et al., "Single and multiple molecular beacon probes for DNA hybridization studies on a silica glass surface," *SPIE* 3602:149-155 (1999).

Francis et al., "Combinatorial libraries of transition-metal complexes, catalysts and materials," *Curr. Opin. Chem. Biol.* 2:422-428 (1998).

Freund and Schapire, "A decision-theoretic generalization of on-line learning and an application to boosting," *J. Computer System Sciences* 55:119-139 (1997).

"Gene Logic and Fujisawa Pharmaceutical sign collaborative discovery research alliance; companies to identify gene expression profiles for diabetes therapeutics," www.genelogic.com, Dec. 2, 1999.

Gold et al., "Diversity of oligonucleotide functions," *Annu. Rev. Biochem.* 64:763-797 (1995).

Golub et al., "Molecular classification of cancer: class discovery and class prediction by gene expression monitoring," *Science* 286:531-537 (1999).

Gygi et al., "Quantitative analysis of complex protein mixtures using isotope-coded affinity tags," *Nature Biotechnol.* 17:994-999 (1999).

Hermann and Patel, "Adaptive recognition by nucleic acid aptamers," *Science* 287:820-825 (2000).

Hollstein et al., "p53 mutations in human cancers," *Science* 253:49-53 (1991).

Hughes et al., "Functional discovery via a compendium of expression profiles," *Cell* 102:109-126 (2000).

Ideker, T., "Statement of Research Interests" (Fall 2000).

Jayasena S., "Aptamers: an emerging class of molecules that rival antibodies in diagnostics," *Clin. Chem.* 45:1628-1650 (1999).

Joyce G., "In vitro evolution of nucleic acids," *Curr. Opin. Struct. Biol.* 4:331-336 (1994).

Kuffner et al., "Pathway analysis in metabolic data bases via differential metabolic display (DMD)," *Bioinformatics* 16:825-836 (2000).

Li and Breaker, "Deoxyribozymes: new players in the ancient game of biocatalysis," *Current Opinion in Structural Biology* 9:315-323 (1999).

Lockhart & Winzeler, "Genomics, gene expression and DNA arrays," *Nature* 405:827-836 (2000).

Lorsch and Szostak, "Chance and necessity in the selection of nucleic acid catalysts," *Acc. Chem. Res.* 29:103-110 (1996).

Marcotte et al., "A combined algorithm for genome-wide prediction of protein function," *Nature* 402:83-86 (1999).

Proux et al., "A pragmatic information extraction strategy for gathering data on genetic interactions," *Proc. Int. Conf. Intell. Syst. Mol. Biol.* 8:279-285 (2000).

Schwikowski et al., "A network of protein—protein interactions in yeast," *Nature Biotechnol.* 18:1257-1261(2000).

Sofia M., "Carbohydrate-based combinatorial libraries," *Mol. Divers.* 2:75-94 (1998).

Sutcliffe et al., "Toga: An automated parsing technology for analyzing expression of nearly all genes," *Proc. Natl. Acad. Sci. USA* 97:1976-1981 (2000).

Suzuki et al., "Insulin resistance associated with decreased levels of insulin-receptor messenger ribonucleic acid: evidence of a de novo mutation in the maternal allele," *J. Clin. Endocrinol. Metab.* 80:1214-1220 (1995).

Taira et al., "Human diabetes associated with a deletion of the tryosine kinase domain of the insulin receptor," *Science* 245:63-66 (1989).

Taylor S., "Lilly lecture: molecular mechanisms of insulin resistance," *Diabetes* 41:1473-1490 (1992).

*Tietz Textbook Clinical Chemistry*, 2nd ed., Burtis and Ashwood, eds., W.B. Saunders Co., Philadelphia, pp. 958-984, 992-997, 1053-1087, 1211-1228, 1320-1350, 1354-1372, 1743-1772, 1887-1913 and 2059-2066 (1994).

*Tietz Textbook Clinical Chemistry*, 3rd ed., Burtis and Ashwood, eds., W.B. Saunders Co., Phildelphia, Chapters 2 and 11-14, pp. 42-72 and 265-355 (1999).

Tohsato et al., "A multiple alignment algoithm for metabolic pathway analysis using enzyme hierarchy," *Proc. Int. Conf. Intell. Syst. Mol. Biol.* 8:376-383 (2000).

Tokino and Nakamura, "The role of p53-target genes in human cancer," *Critical Reviews in Oncology/Hematology* 33:1-6 (2000).

Tuerk and Gold, "Systematic evolution of ligands by exponential enrichment: RNA ligands to T4 DNA polymerase," *Science* 249:505-510 (1990).

van Someren et al., "Linear modeling of genetic networks from experimental data," *Proc. Int. Conf. Intell. Syst. Mol. Biol.* 8:355-366 (2000).

Walt D., "Bead-based fiber-optic arrays," *Science* 287:451-452 (2000).

Wang X., "Role of p53 and apoptosis in carcinogenesis," *Anticancer Research* 19:4759-4771 (1999).

Yona and Levitt, "Towards a complete map of the protein space based on a unified sequence and structure analysis of all known proteins," *Proc. Int. Conf. Intell. Syst. Mol. Biol.* 8:395-406 (2000).

Zien et al., "Analysis of Gene Expression Data with pathway scores," *Proc. Int. Conf. Intell. Syst. Mol. Biol.* 8:407-417 (2000).

Timecourse Data: Metabolic Chart, http://cmgm.stanford.edu/pbrown/explore/metachart.html: pp. 1-2 (2000).

Product Description: "GeneSpring Lite," Silicone Genetics website, http://www.signetics.com/Products/GeneSpring/Overlays.htm updated as of Feb. 29, 2000.

* cited by examiner

GENE DISCOVERY FOR THE SYSTEM ASSIGNMENT OF GENE FUNCTION

BACKGROUND OF THE INVENTION

This invention relates generally to genome-wide analysis and, more specifically, to a method of determining the function of a gene.

The Human Genome Project, by cataloging the sequences of the estimated 100,000 human genes, provides a first step in understanding humans at the molecular level. However, with the completion of the sequencing phase of the project, many questions remain unanswered, including what roles most of these genes play in cells and how the genes work together to perform functions in cells. The answers to these questions will lead to important advances and developments in both research and medicine.

Exemplified by genome sequencing projects, discovery science enumerates all the genes or encoded products of a genome without concern for their functional characteristics and cellular roles. The Human Genome Project and other large scale sequencing projects have fueled technological advances in discovery science. Large-scale gene sequencing, gene expression analysis methods, such as DNA microarrays, and proteomics methods have facilitated the accumulation of an enormous amount of data describing the sequences and expression levels of virtually every gene in organisms such as, the bacterium *Escherichia coli*, the yeast *Saccharomyces cerevisiae*, the worm *Caenorhabditis elegans*, as well as more complex organisms such as humans. Volumes of sequence and expression data can be obtained from virtually any cell or organism. However, standing alone, these volumes of sequence and expression data are difficult to interpret and apply to accurately predicting cellular functions of genes and their products, their interplay within a cell, or their dynamics in response to change.

Over the past several years, researchers have attempted to understand and characterize functions of the many newly identified genes having unknown cellular roles by testing experimental hypotheses. Such hypothesis-driven research to determining the function of an uncharacterized gene, or its encoded product, typically involves formulating a working hypothesis based on empirical observations provided by sequence comparisons and experimental data. The working hypothesis is then tested experimentally to determine if a proposed function is correct. The process is revised and repeated until experimental results are consistent with the working hypothesis of the proposed cellular function. Such an approach is labor-intensive, time-consuming and constrained by available functional information.

One reason for the difficulties in determining functions of uncharacterized genes and their products using a hypothesis driven research approach is that the observations which form the foundation of the working hypothesis and the investigated genes are viewed in an isolated or static manner. These views can result from either a lack of available information or from practical consideration which preclude analysis of the dynamic interplay of the other numerous genes and molecules in the cell. Absent such knowledge or assessment of the various relationships, the reference point or context in which to interpret experimental results can be misconstrued, viewed too narrowly or, perhaps too broadly.

Thus, there exists a need for methods which assimilate biological information to predict gene function. The present invention satisfies this need and provides related advantages as well.

SUMMARY OF THE INVENTION

The invention provides a method for assigning a cellular function to a component of a biochemical system. The method involves (a) determining a multidimensional shape space for one or more components of a biochemical system in a reference state; (b) perturbing a component within said biochemical system; (c) determining a perturbed multidimensional shape space for one or more components of a pathway in said perturbed biochemical system, and (d) identifying a multidimensional coordinate point corresponding to a component of said perturbed pathway altered between reference and perturbed multidimensional shape spaces, said identified component being assigned a cellular function of said perturbed pathway.

In another embodiment, the method involves (a) determining an integrated multidimensional data space for each of at least two networks in a reference state biochemical system; (b) determining a multidimensional shape space for at least one network in a perturbed state biochemical system, and (c) determining a component multidimensional coordinate point contained within a multidimensional shape space representing the difference between multidimensional data spaces of reference and perturbed states of said biochemical system, said component being linked to said network having perturbed multidimensional shape space, and thereby being assigned the cellular function of said network.

In a further embodiment, the method involves (a) comparing two integrated multidimensional data spaces of a biochemical system obtained in reference and perturbed states of a biochemical system, said integrated multidimensional data spaces comprising at least two networks, and (b) determining a component multidimensional coordinate point contained within a multidimensional data space representing the difference between multidimensional data spaces of reference and perturbed states of said biochemical system, said component being linked to said network having said perturbed multidimensional shape space, and thereby being assigned a cellular function of said network.

In an additional embodiment, the method involves (a) perturbing a component of a network in a reference biochemical system; (b) determining a multidimensional coordinate point representing a data element of one or more components of a perturbed biochemical system; (c) comparing said multidimensional coordinate point to a reference data element region, and (d) determining if said multidimensional coordinate point is within or outside said reference data element region, wherein a multidimensional coordinate point outside of said reference data element region indicates that said component is linked to said perturbed biochemical network, and is thereby assigned a cellular function of said network.

DETAILED DESCRIPTION OF THE INVENTION

Figure 1:
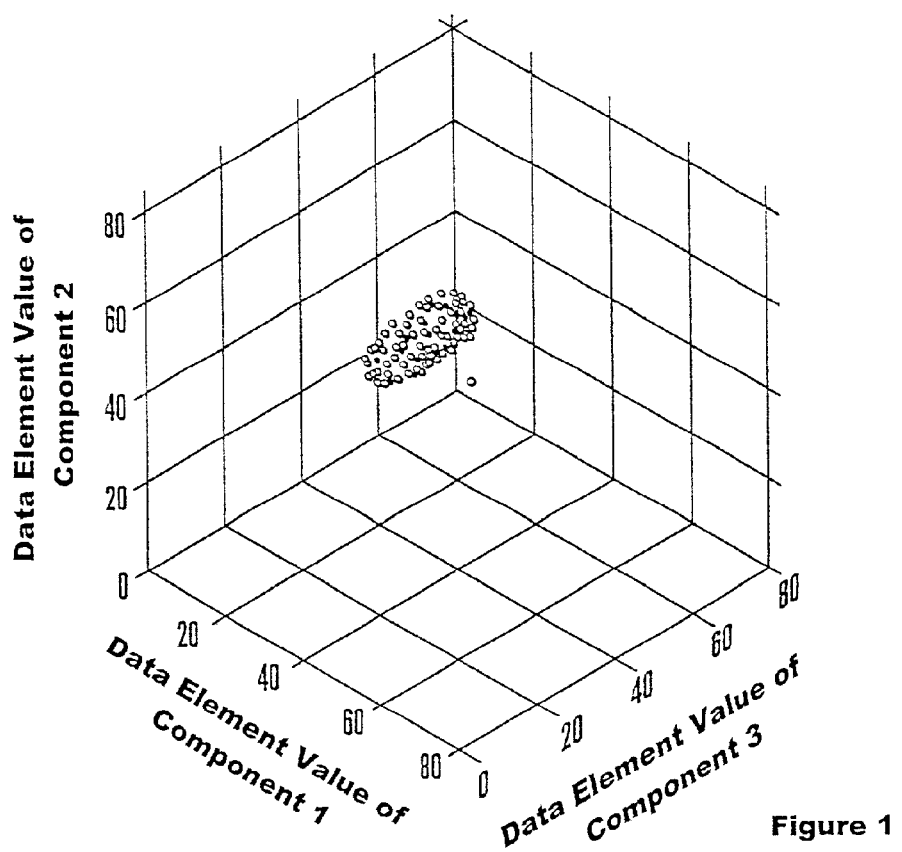
FIG. 1 shows a schematic diagram of a hypothetical network-associated reference data element region. The circles represent multidimensional coordinate points representative of the values of data elements (in arbitrary units) of three components of a biochemical system. Shown is a network-associated reference data element region of a reference biochemical system in three-dimensional space as a region of coordinate points and the coordinate point of a perturbed biochemical system that lies outside the network-associated reference data element region.
Figure 2:
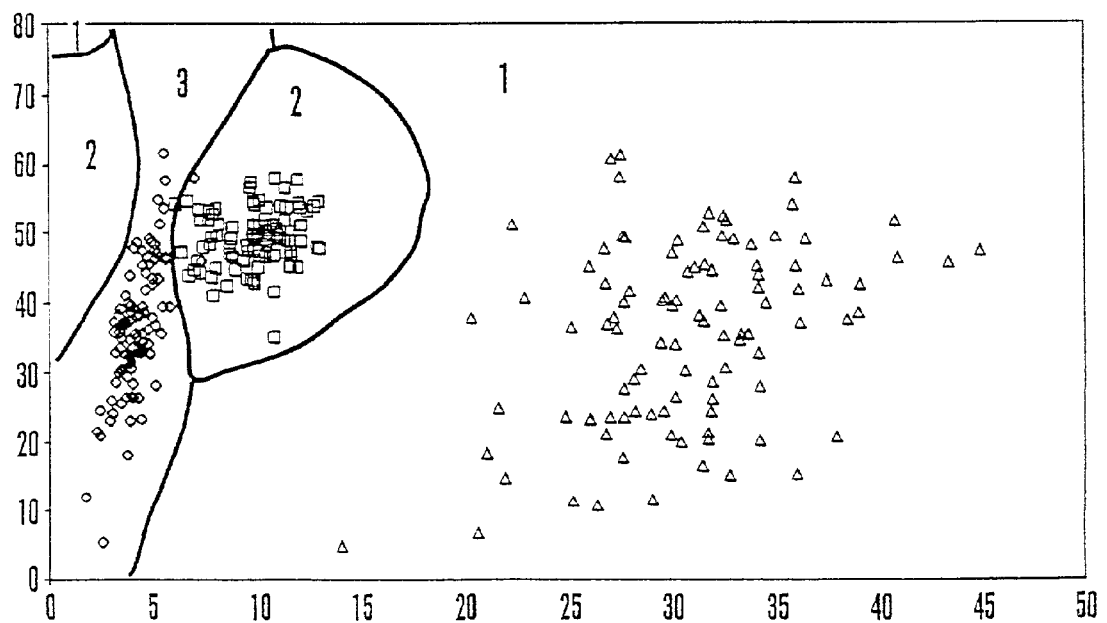
FIG. 2 shows the coordinate points in two-dimensional space representative of the data element levels (in arbitrary units) of two components. The data set shows three states of a biochemical system that can be classified in three regions, corresponding to three reference network-associated data element regions.

This invention is directed to methods for assigning a cellular function to a component of a biochemical system. The methods involve using multidimensional shape spaces to describe components of a biochemical system as they function in a particular state of the biochemical system. Multidimensional shape spaces contain multidimensional coordinate points, each of which represents a characteristic of one or more individual components of the biochemical system. For example, a multidimensional coordinate point can represent the expression of a gene, comparative expression of a gene with other genes, or expression of two or more genes. The ability to represent more than one gene using a multidimensional coordinate point is useful when analyzing global measurements of biochemical system components, such as when global expression analysis includes from some to substantially all expressed genes in a cell or tissue.

Information about the cellular functions of genes in a biochemical system is obtained by perturbing a component of the biochemical system and determining the difference between the multidimensional shape spaces of the reference and perturbed systems. Because genes and their protein products function together in a biochemical system, such as a cell, perturbation of a gene will have some cellular consequence, such as altered expression or activity of another component of the system. Perturbation of a particular gene, for example, can result in a change in the function of the biochemical pathway of the gene, or can result in a global change in the function of one or more pathways or networks. For example, perturbation of a gene encoding an enzyme of a metabolic pathway can result in both altered function of down-stream enzymes in the same pathway, as well as up-regulation of genes in other pathways and networks that compensate for the loss of function of the perturbed metabolic pathway. Multidimensional shape space can provide a global view of the effect of perturbing a particular gene because it can contain multidimensional coordinate points corresponding to, for example, members of the perturbed pathway, compensatory pathways, and other pathways and networks possibly altered by the perturbation. Multidimensional shape space also can provide a focused view of the effect of perturbing a particular gene, depending on the contents of the multidimensional shape space, because multidimensional shape space can be used to describe systems, subsystems, networks, pathways and single components. For example, the method can be used to determine the function of components acting together as a system or subsystem, as well as used to dissect the function of such multi-component systems down to small groups, such as networks and pathways, as well as for determining the function of a single component within the analyzed system.

One advantage of using multidimensional shape space is that the comparison allows detection and analysis of changes within the system that lack an overt phenotype or are otherwise difficult to reliably measure. For example, the effects of gene knock-out that lacks a detectable phenotype in an animal can be determined using multidimensional shape space.

The methods for assigning a cellular function to a gene involve determining changes between a reference and perturbed biochemical system, such as changes in mRNA or protein expression of system components. Rather than determining these changes using standard mathematical methods, multidimensional shape space can then be used to probe, quantitate and analyze these changes with increased sensitivity. Changes identified in multidimensional shape space can be used to assign genes or groups of genes into pathways and networks. Assignment of cellular function to an uncharacterized gene can be made based in its assignment to a particular pathway or network and functional location within that pathway or network.

To use the information contained in a multidimensional shape space for assigning a function to a perturbed gene requires no prior prediction or knowledge of the cellular function of a perturbed gene. On the contrary, differences between reference and perturbed multidimensional shape spaces reveal multidimensional coordinate points corresponding to components altered by the perturbation, and a cellular function can be assigned to the perturbed gene based on a cellular function assigned to another perturbed component, or group of components. Among the multidimensional coordinate points altered by a perturbation will be those that correspond to components contained in a common pathway and network, including components having both known and unknown cellular functions. For example, if perturbation of a gene results in a change in a multidimensional coordinate point corresponding to a component of a pathway, or group of components of a pathway, that gene can be considered to function within the pathway, and the perturbed gene is assigned the cellular function of the pathway. Similar analysis can be performed on the components of the pathway to identify the actual function of the initially perturbed or targeted gene. The assignment of a component to a particular pathway or network can be corroborated, for example, by perturbing a second component of the pathway, or by making a second perturbation of the component. Similarly, as discussed further below, a variety of perturbations can also be made to initially identify networks, pathways and their constituent components. The target gene can be assigned to its corresponding pathway or network based on its reaction to these perturbations to identify its function.

The methods of the invention for assigning a cellular function to a gene are applicable to analysis of small and large data sets, and to simple and complex organisms, because a multidimensional coordinate point can describe as few as two components, several components, tens of components, or even hundreds of components, depending on the complexity of the biochemical system. For example, in a highly complex biochemical system such as a mouse, multidimensional coordinate points can each reflect characteristics, such as expression levels, of substantially all genes expressed in the animal, by representing sets of components by multidimensional coordinate points. Accordingly, the methods can be used to assign a function to a few genes, to many genes, or to substantially all genes expressed in a mouse or other complex organism, such as a human.

Multidimensional coordinate points can be used to represent two or more components of a system. The two or more components can be selected for inclusion in a single multidimensional coordinate point either randomly or purposefully. For example, when performing a system analysis, components can be randomly divided into groups, each group to be represented by a single multidimensional coordinate point. Alternatively, particular components known to participate in a common function can be contained in a common network or pathway, or be otherwise functionally associated, can be placed into a group to be represented by a single multidimensional coordinate point. When such functionally related components are grouped together into a multidimensional coordinate point, a change in that point can be diagnostic for a perturbation that affects the represented cellular function. For example, a multidimensional coordinate point representing five components of a mitosis pathway would be altered upon perturbation of a sixth component of the pathway. In this specific example, if the perturbation was a knock-out of an uncharacterized gene, alteration in the mitosis-associated multidimensional coordinate point would indicate that the uncharacterized gene functions as an additional component in the pathway.

The process of assigning functions to genes, from one to many to substantially all genes, in a complex organism, such as a mouse, can have several starting points. One useful method involves determining a multidimensional shape space representing characteristics, such as mRNA or protein levels, of substantially all components in a cell from an unperturbed mouse. Multidimensional shape spaces also can be determined for various cell types of an unperturbed mouse, when assigning functions to multiple genes is desired. The use of multidimensional data spaces obtained for different cell types will allow analysis of genes that function only in a particular cell type, such as a neuronal cell-specific gene, as well as genes that function differently in different cell types. Multidimensional shape spaces determined using cells from an unperturbed mouse are referred to as reference multidimensional shape spaces, and are compared to perturbed multidimensional shape spaces determined using cells from a perturbed mouse.

As the cellular function of a gene is determined by its interrelationship with at least one other system component, this interrelationship being revealed by comparing reference and perturbed multidimensional data spaces, the method involves perturbing a gene and examining the effect of the perturbation by comparing multidimensional data spaces determined for cells from normal and perturbed organisms, cells or other biochemical systems, including animals. Exemplary useful perturbations are a gene knock-out or other mutation that destroys function, which provide the advantage of being specific for one particular gene. The perturbed multidimensional shape space of a mouse cell in which the gene is normally expressed will contain a multidimensional coordinate point representing the knocked-out gene, the value of which will be changed from a reference value. Other multidimensional coordinate points altered between reference and perturbed multidimensional shape spaces can be identified, each of these points corresponding to at least one other system component having altered expression in response to the gene knock-out. The identity of a system component having such altered expression is determined, for example, by its DNA sequence. If the component is known or suspected to be contained in a particular pathway or network, the component is assigned the cellular function of that pathway or network. The component perturbed by knock-out also is assigned that cellular function because a relationship between the two components has been established by alteration of the pathway component multidimensional coordinate point in response to knock-out of the component. In a case where multiple multidimensional coordinate points are identified to be altered in a perturbed multidimensional space shape, the knock-out gene preliminarily can be assigned the function of a gene or genes represented by one of the altered multidimensional coordinate points, and a further gene knock-out or other perturbation can be used to corroborate the assignment.

Further gene knock-outs of components can be selected systematically, for example, to corroborate inclusion of a component in a particular pathway by perturbing other pathway components. A second component to be perturbed by knock-out can be, for example, a component known or suspected to function in the pathway or network of a gene or genes represented by an altered multidimensional coordinate point. Additional gene knock-outs of components known or suspected to function in such a pathway can be performed to further corroborate the assignment of the perturbed component to that pathway, as well as to deduce a more specific function of the perturbed component. For example, such perturbations can be used to deduce that a perturbed component functions in a pathway directly upstream or downstream from another component.

Alternatively, knock-out of substantially all genes in a mouse will necessary reveal multidimensional shape spaces corresponding to specific pathways and networks without the need to make an initial assignment of a component to a network. These pathway and network multidimensional shape spaces will be revealed by comparing reference and perturbed multidimensional shape spaces for each component knock-out, and determining which component knock-outs have similar or over-lapping areas of multidimensional shape space altered.

Multidimensional coordinate points representing components of a network are grouped together to form a multidimensional shape space. A multidimensional shape space can be used to represent the components of a biochemical pathway, for example, a signal transduction pathway or gene expression regulatory pathway; a biochemical network, for example, a group of molecules that function together in cell adhesion, mitosis or glucose uptake; or a biochemical system, for example, a cell, organ or animal. Multidimensional shape spaces can be used as sensitive indicators of biochemical system function because each multidimensional coordinate point reflects a relationship of one component with anywhere from one other component, to several components, to hundreds of components, to substantially all components in the system.

In one embodiment, the methods of the invention involve linking together components of a biochemical system into groups that participate in a common cellular function. The methods can be used to expand a group of components known to function in a biochemical pathway or network, as well as to assign a cellular function to an uncharacterized gene. The methods involve using mathematical and statistical methods to link together components of a biochemical system, by at least one shared characteristic, such as by both components having altered gene expression under a particular perturbed state of a biochemical system.

In another embodiment, the method involves determining a component multidimensional coordinate space for a component of a biochemical system. The component multidimensional coordinate space represents a characteristic of the component, such as an expression level, relative to that of other components of the system. For example, in a biochemical system containing 100 components, a component multidimensional coordinate space can represent a comparison of the mRNA expression of one component with mRNA expression of the other 99 components of the system, each value representing a difference in expression being a parameter in multidimensional space. A component multidimensional coordinate space can therefore describe a large number of relative mRNA expression values in a single value.

In addition, component multidimensional coordinate spaces contain relative data elements values that can be determined without any need for an internal control. Component multidimensional coordinate spaces of two or more components can be contained in multidimensional shape space, which can be used to describe a pathways, networks and biochemical systems. A single change in a biochemical system, such as a change in expression of one gene, becomes amplified in multidimensional shape space because a changed expression value is a changed parameter in each component multidimensional coordinate space in the multidimensional shape space of the pathway, network or system. Therefore, by observing changes in a multidimensional shape space that occur when a biochemical system is perturbed, the relationships between components of the system become readily apparent.

In another embodiment, the methods of the invention involve determining an integrated multidimensional data space. An integrated multidimensional data space provides a framework for observing changes in multidimensional shape space by constraining the shape space by a second parameter. Although the second parameter need not be the same for each component represented in an integrated multidimensional data space, one example of preparing an integrated multidimensional data space for a large data set of multidimensional coordinate points corresponding to gene expression values, is to retain only those points that correspond to components that physically interact. The resulting integrated multidimensional data space would represent only components that are linked together by two parameters, each component then determined to be a member of at least one biochemical network.

In a further embodiment, the method involves determining a multidimensional coordinate point representing data elements of a set of two or more components of a biochemical network. Such a multidimensional coordinate point can be compared with a statistically determined region representing a reference multidimensional coordinate point corresponding to the data elements of the same set of two or more components in a biochemical system. The methods can be used in a multiparameter analysis by measuring a data element, such as an expression level, for each of multiple components representative of a reference state of a biochemical system.

As used herein, the term "multidimensional coordinate point" refers to a coordinate defined by "n" parameters, where n is the number of components in a biochemical system, or subset thereof, and each parameter is a data element of a component of the biochemical system, or subset thereof. Therefore, a multidimensional coordinate point representative of a data element of two components is defined by two parameters corresponding to values representative of data elements of the two components. Similarly, a multidimensional coordinate point representative of data elements of three molecules is defined by three parameters corresponding to values representative of the data elements of the three components (see FIG. 1). A multidimensional coordinate point representative of the data elements of n components is defined by n parameters corresponding to the values of the data elements of n components. Therefore, multidimensional coordinate points for a group of components such as the components of a pathway, network or biochemical system is found in n-dimensional shape space. As such, the term "multidimensional shape space" is intended to mean a set of multidimensional coordinate points for a group of components of a pathway, network or biochemical system.

As used herein, the term "component multidimensional coordinate space," refers to a set of "n" parameters that collectively define a "multidimensional coordinate point" for a component, where n is the number of components in a biochemical or constituent system, network or pathway, and each parameter is the value of a data element of the component relative to the value of a data element of another component in the biochemical or constituent system. Therefore, a component multidimensional coordinate space defined by two parameters corresponds to the value of a data element of the component relative to the value of a corresponding data element of another component. Similarly, a component multidimensional coordinate space defined by three parameters corresponds to the value of a data element of the component relative to the values of corresponding data elements of two other components. A component multidimensional coordinate space defined by n parameters corresponds to the value of a data element of a component relative to the values of corresponding data elements of n−1 other components.

As used herein, the term "integrated multidimensional data space" is intended to mean a multidimensional shape space corresponding to a set of components linked by two or more data elements, when at least one data element is represented by a multidimensional coordinate point.

As used herein, the term "region," when used in reference to a data element of a component, refers to a region of multidimensional space classified using one or more statistical methods. An unperturbed state-associated reference data element region is a region of multidimensional space determined by values of data elements, such as data elements representing expression levels, of a sample of molecules, and the boundaries of the region represent the perturbation limit, outside of which indicates that an individual has a perturbed multidimensional coordinate point that lies outside the statistical boundaries of the reference population. A biochemical system with a perturbed multidimensional coordinate point, with a level of expression that lies outside the interval determined from reference individuals, potentially has a perturbed state biochemical system. Similarly, a network-associated reference data element region is a region of multidimensional space determined by values of data elements of a sample of molecules, and the boundaries of the region represent the perturbation limit, outside of which indicates that a biochemical system has a multidimensional coordinate point that lies outside of the statistical boundaries of an unperturbed network.

The region represents a classification of data elements that is representative of a reference state of a biochemical system and is useful for predicting the function of a gene. Exemplary statistical methods include, for example, discriminate analysis, classification analysis, cluster analysis, analysis of variance (ANOVA), regression analysis, regression trees, decision trees, nearest neighbor algorithms, principal components, factor analysis, multidimensional scaling and other methods of dimensionality reduction, likelihood models, hypothesis testing, kernel density estimation and other smoothing techniques, cross-validation and other methods to guard against overfitting of the data, the bootstrap and other statistical resampling techniques, artificial intelligence, including artificial neural networks, machine learning, data mining, and boosting algorithms, and Bayesian analysis using prior probability distributions.

As used herein, the term "reference data element region" is intended to mean a region of multidimensional space that is representative of a data element of a component, or of a multidimensional coordinate point representing two or more components, determined for at least two equivalent biochemical systems in a reference state. Equivalent biochemical systems are biochemical systems, such as an organism, organ, tissue, cell or subcellular system, treated in an identical manner. Exemplary equivalent biochemical systems include two cells of the same type obtained from one individual, or from two related individuals, or from two unrelated individuals. A "reference data element region" can be used to determine if a perturbation of a biochemical system results in alteration of a data element or multidimensional coordinate point corresponding to components of a biochemical system. A determination that a component multidimensional coordinate is altered in response to perturbing a particular network or pathway can be used to assign to the component the cellular function of the perturbed network or pathway.

As used herein, the term "biochemical system" is intended to mean a group of interacting, interrelated, or interdependent molecules that form a functional biochemical unit such as, for example, an organism, organ, tissue, cell or subcellular system. As used herein, the term "constituent system" refers to a biochemical system that is a subset of a biochemical system. A constituent system of an organism can be, for example, an organ, tissue or cell. Similarly, a constituent system of a cell can be a subcellular system such as, for example, an organelle or a cellular fraction, such as a nuclear, cytoplasmic or membrane fraction. A constituent system of a cell also can include subcellular systems such as an electron-transfer chain, a signal transduction cascade, a cytoskeleton, translation machinery, a secretory pathway, a nuclear pore complex, a nuclear scaffold, chromatin, transcriptional machinery and RNA processing machinery, DNA recombination machinery, and metabolic networks or pathways. A subcellular system can be contained in, for example, a cell, a cellular fraction or it can be substantially isolated. Groups of components which make up subcellular systems that form functional units are also included within the meaning of the term constituent system.

As used herein, the term "network" is intended to mean a group of interacting, interrelated, or interdependent molecules that consist of at least two biochemical pathways and function in common category of biochemical function. Therefore, a network is a higher order subcellular system made up of two or more constituent pathway systems that act together in order to effect one or more activities within a common functional category which characterizes the constituent pathways of the network. Acting together includes, for example, concerted functionally dependent relationships and interactions such as physical interactions, biosynthetic alterations, metabolic alterations or regulatory signals between at least one component molecule within two pathways. Such concerted actions can occur, for example, simultaneously or over time and can be proximal or distal in space compared to the reference molecule or pathway. Other types of interactions, interrelationships or interdependencies, also can occur and are well known to those skilled in the art. The number of concerted functionally dependent relationships and interactions can be small such as a single or a few common components or signals between two pathways of the network, or, the number can be large and include several to many interactive, interrelated or interdependent components between two or more pathways within a network.

A network also can contain one or more components that function in one or more categories of biochemical function in addition to functioning in the specific category of the network. A category of cellular function refers to a type of cellular process, such as respiration, amino acid synthesis, protein synthesis, RNA synthesis, RNA processing, glycolysis, glycogen metabolism, morphogenesis, stress response, cell death, calcium uptake, mitochondrial function, organization of intracellular transport vesicles, and organization of cytoskeleton.

As used herein, the term "pathway" is intended to mean a set of system components involved in two or more sequential molecular interactions that result in the production of a product or activity. A pathway can produce a variety of products or activities that can include, for example, intermolecular interactions, changes in expression of a nucleic acid or polypeptide, the formation or dissociation of a complex between two or more molecules, accumulation or destruction of a metabolic product, activation or deactivation of an enzyme or binding activity. Thus, the term "pathway" includes a variety of pathway types, such as, for example, a biochemical pathway, a gene expression pathway and a regulatory pathway. Similarly, a pathway can include a combination of these exemplary pathway types.

A biochemical pathway can include, for example, enzymatic pathways that result in conversion of one compound to another, such as in metabolism, and signal transduction pathways that result in alterations of enzyme activity, polypeptide structure, and polypeptide functional activity. Specific examples of biochemical pathways include the pathway by which galactose is converted into glucose-6-phosphate and the pathway by which a photon of light received by the photoreceptor rhodopsin results in the production of cyclic AMP. Numerous other biochemical pathways exist and are well known to those skilled in the art.

A gene expression pathway can include, for example, molecules which induce, enhance or repress expression of a particular gene. A gene expression pathway can therefore include polypeptides that function as repressors and transcription factors that bind to specific DNA sequences in a promoter or other regulatory region of the one or more regulated genes. An example of a gene expression pathway is the induction of cell cycle gene expression in response to a growth stimulus.

A regulatory pathway can include, for example, a pathway that controls a cellular function under a specific condition. A regulatory pathway controls a cellular function by, for example, altering the activity of a system component or the activity of a biochemical, gene expression or other type of pathway. Alterations in activity include, for example, inducing a change in the expression, activity, or physical interactions of a pathway component under a specific condition. Specific examples of regulatory pathways include a pathway that activates a cellular function in response to an environmental stimulus of a biochemical system, such as the inhibition of cell differentiation in response to the presence of a cell growth signal and the activation of galactose import and catalysis in response to the presence of galactose and the absence of repressing sugars.

The term "component" when used in reference to a biochemical system, network or pathway is intended to mean a molecular constituent of the biochemical system, network or pathway, such as, for example, a polypeptide, nucleic acid, other macromolecule or other biological molecule.

As used herein, the term "polypeptide" when used in reference to a component of a biochemical system, is intended to mean two or more amino acids covalently bonded together. A polypeptide can be modified by naturally occurring modifications such as post-translational modifications, including phosphorylation, lipidation, prenylation, sulfation, hydroxylation, acetylation, addition of carbohydrate, addition of prosthetic groups or cofactors, formation of disulfide bonds, proteolysis, assembly into macromolecular complexes, and the like. A polypeptide can also contain minor modifications such as, for example, conservative substitutions of naturally and non-naturally occurring amino acids, amino acid analogs and functional mimetics. For example, Lysine (Lys) is considered to be a conservative substitution for the amino acid Arginine (Arg). Non-naturally occurring amino acids include, for example, (D)-amino acids, norleucine, norvaline, ethionine and the like. Amino acid analogs include modified forms of naturally and non-naturally occurring amino acids. Such modifications can include, for example, substitution or replacement of chemical groups and moieties on the amino acid or by derivitization of the amino acid. Amino acid mimetics include, for example, organic structures which exhibit functionally similar properties such as charge and charge spacing characteristic of the reference amino acid. Those skilled in the art know or can determine what structures constitute functionally equivalent amino acid analogs and amino acid mimetics.

As used herein, the term "nucleic acid" when used in reference to a component of a biochemical system, is intended to mean two or more nucleotides covalently bonded together such as deoxyribonucleic acid (DNA) or ribonucleic acids (RNA) and including, for example, single-stranded and a double-stranded nucleic acid. The term is similarly intended to include, for example, genomic DNA, cDNA, mRNA and synthetic oligonucleotides corresponding thereto which can represent the sense strand, the anti-sense strand or both. As with polypeptide components of a system, nucleic acid components similarly can include natural and non-naturally occurring modifications such as post-transcriptional modifications, minor substitutions and incorporation of functionally equivalent nucleotide analogs and mimetics. Such changes and methods of incorporation are well known to those skilled in the art.

Other biological molecules that are included within the meaning of the term "component" can be include, for example, macromolecules and organic and inorganic molecules that are constituents of a biochemical system. Macromolecules other than polypeptides and nucleic acids that are constituents of a biochemical system, network or pathway include, for example, lipids and carbohydrate as well as combinations of macromolecules such as glycoproteins, protoglycans, glycolipids and the like. Organic molecular constituents can include, for example, a sugar or modification thereof such as glucose or its various phosphate or acetylated derivatives. Other sugars include, for example, maltose, galactose, fructose, and xylose, derivatives thereof, and metabolites thereof, such as lactate and pyruvate. Organic molecular constituents additionally include polycyclic compounds such as steroids; building blocks of macromolecules such as nucleotides, nucleosides, amino acids, lipids, and fatty acids. Neurotransmitters such as acetylcholine and dopamine are additional examples of molecules that are constituents of a biochemical system. Exemplary inorganic and small molecules that are constituents of a biochemical system include salts, ions, and metals such as sodium, potassium, chloride, calcium, bicarbonate/$CO_2$, chromium, iron, and the like. Various other macromolecules, organic and inorganic molecules, are well known to those skilled in the art as constituents of a biochemical system, network or pathway. All of such constituents are intended to be included within the meaning of the term component as it is used herein.

As used herein, the term "data element" is intended to mean a value or other analytical representation of factual information that describes a characteristic or a physicochemical property of a biochemical system or a component of a biochemical system. A data element can be represented for example, by a number, "plus" and "minus" symbols, a particular hue or saturation of color, a geometric shape, a set of coordinates, a word, an alphanumeric string or any other descriptive form or form suitable for computation, analysis, or processing by, for example, a computer or other machine or system capable of data integration and analysis.

A data element can represent a property of a biochemical system component. For example, representations of accumulated or non-steady-state levels of nucleic acid and protein expression of a system component can be data elements. Therefore, the term "expression data element" refers to a value that represents a direct, indirect or comparative measurement of the level of expression of nucleic acid or polypeptide of a system component.

A data element can further be a representation of a physical interaction of a system component, such as, for example, a polypeptide-polypeptide interaction, nucleic acid-polypeptide interaction, nucleic acid-nucleic acid interaction, or other direct binding interaction between a polypeptide or nucleic acid with another biological molecule. Therefore, a physical interaction data element refers to a value or symbol that represents a physical interaction, such as a direct binding interaction of one component with another component.

A data element of a biochemical system component also can include, for example, a representation of a global property of the biochemical system. For example, a cell metabolic rate, growth rate or a cellular phenotype of a biochemical system under a specified condition, can be represented by a data element.

As used herein, the term "perturbed condition" when used in reference to a biochemical system, is intended to mean an alteration of a biochemical state or circumstances imposed on a biochemical system compared to a reference or normal state or circumstances of the biochemical system. A perturbation, to effect a perturbed condition, can include, for example, any physical modification or treatment of the biochemical system as well as exposure to any stimulus. Therefore, a perturbation can include, for example, genetic alterations, contact with macromolecules, compounds, agents and drugs, and exposure to changes in and environmental stimuli or procedural manipulations of a biochemical system.

Genetic changes useful for perturbing a biochemical system include, for example, modifications which alter the expression of a system component. Such modifications can include genetic changes that directly act on one or more system components and increase or decrease their expression. Alternatively, genetic modifications can indirectly act on one or more system components and affect their expression. For example, direct genetic changes include system component gene deletions and alterations, such as mutations or truncations that destroy or alter the expression level of a system component. Additionally, such alterations can include both increases and decreases in expression of the modified gene. Direct genetic changes are also useful for perturbing the activity or physical interactions of a system component. Indirect genetic changes useful for perturbing the expression level of a system component include, for example, deletions and alterations of regulatory elements of a system component gene and of genes encoding products that regulate the expression or are otherwise upstream components which affect the expression of a system component. Similarly, indirect genetic changes are also useful for perturbing the activity or intermolecular interactions, for example, of a system component. Other genetic changes exist as well and are well known to those skilled in the art.

Environmental changes useful for perturbing expression, activity, physical interactions or other characteristics or properties of a system component include, for example, a change in growth conditions, a temperature change, a treatment such the addition or removal of a component of growth medium, and treatment with a compound, drug, light, radiation, or other agent. Other environmental changes exist as well and are well known to those skilled in the art.

The term "perturbation state" when used in reference to a biochemical system or network, is intended to mean the characterization of the biochemical system under a specified perturbed condition.

The term "physical interaction" is intended to mean a direct binding association between two or more components of a biological system. A physical interaction includes, for example, polypeptide-polypeptide, polypeptide-nucleic acid, nucleic acid-nucleic acid interactions and interactions of other biological molecules with polypeptides and nucleic acids. A physical interaction includes, for example, binding between signal transduction components or a receptor and ligand, and the formation of a stable complex, such as that between two subunits of an enzyme that remain associated under specified conditions. Additionally, a physical interaction includes, for example, both covalent interactions, such as those between polypeptides joined by a disulfide bond, and non-covalent interactions, such as those between a transcription factor and its nucleic acid substrate. A physical interaction between two components of a system can be determined by a variety of methods well known in the art, including, for example, direct measurement, computational analysis and by probing data bases reporting such information.

The term "functionally interactive" when used in reference to a component of a biochemical system, is intended to mean a system component that exhibits two or more biochemically relevant interactions, relationships, or dependencies with another component of the biochemical system. Therefore, a functionally interactive component of a biochemical system identifies such a component as a member of at least one network or pathway of the biochemical system.

As used herein, the term "expression level" is intended to mean the amount, accumulation or rate of synthesis of a biochemical system component. The expression level of a component can be represented, for example, by the amount or synthesis rate of messenger RNA (mRNA) encoded by a gene, the amount or synthesis rate of polypeptide corresponding to a given amino acid sequence encoded by a gene, or the amount or synthesis rate of a biochemical form of a molecule accumulated in a cell, including, for example, the amount of particular post-synthetic modifications of a molecule such as a polypeptide, nucleic acid or small molecule. The meaning of the term "expression level" can be used to refer to an absolute amount of a molecule in a sample or to a relative amount of the molecule, including amounts determined under steady-state or non-steady-state conditions. The expression level of a molecule can be determined relative to a control component molecule in a sample.

A nucleic acid expression level of a molecule is intended to mean the amount, accumulation or rate of synthesis of a RNA corresponding to a gene component of a biochemical system. The gene expression level can be represented by, for example, the amount or transcription rate of hnRNA or mRNA encoded by a gene. A nucleic acid expression level similarly refers to an absolute or relative amount or a synthesis rate determined, for example, under steady-state or non-steady-state conditions.

A polypeptide expression level is intended to mean the amount, accumulation or rate of synthesis of a biochemical form of a polypeptide expressed in a biochemical system. The polypeptide expression level can be represented by, for example, the amount or rate of synthesis of the polypeptide, a precursor form or a post-translationally modified form of the polypeptide. Various biochemical forms of a polypeptide resulting from post-synthetic modifications can be present in a biochemical system. Such modifications include post-translational modifications, proteolysis, and formation of macromolecular complexes. Post-translational modifications of polypeptides include, for example, phosphorylation, lipidation, prenylation, sulfation, hydroxylation, acetylation, addition of carbohydrate, addition of prosthetic groups or cofactors, formation of disulfide bonds and the like. Accumulation or synthesis rate with or without such modifications is included with in the meaning of the term. Similarly, a polypeptide expression level also refers to an absolute amount or a synthesis rate of the polypeptide determined, for example, under steady-state or non-steady-state conditions.

As used herein, the term "pathological condition" is intended to mean a disease or abnormal condition, including an injury, of a mammalian cell or tissue. Such pathological conditions include, for example, hyperproliferative and unregulated neoplastic cell growth, degenerative conditions and infectious diseases. Numerous other abnormal or aberrant conditions are well known in the art and are included within the meaning of the term as it is used herein.

In one embodiment, the methods of the invention involve assigning a cellular function to a gene based on the behavior of the gene or a corresponding gene product. Such behavior can be assessed by determining if a multidimensional coordinate point representing the gene or gene product is altered when the biochemical system is perturbed. To determine if a multidimensional coordinate point representing a component is altered in a perturbed state of a biochemical system, the value of the point is compared with that of a reference system. A significant difference between the multidimensional coordinate point representing a component under two different conditions of a biochemical system indicates that the component has an interaction, interrelation or interdependency with another component contained in a pathway or network of components perturbed in the perturbed state of the biochemical system. The method can be used to determine cellular functions for a single gene. Groups of related or unrelated genes, including those contained in pathways and network, and substantiate all genes in a biochemical system or subsystem.

In another embodiment, the methods of the invention involve assigning a cellular function to a gene based on the behavior of a set of components in a biochemical network or pathway. Biochemical networks and pathways contain components that function in concert, for example, by regulating each others activity or expression. Data elements describing components of biochemical networks and pathways, such as levels of mRNA or protein expression, are changed in predictable, as well as unrecognized, ways depending on the state of a biochemical system. For example, pathway or network genes can be up-regulated or down-regulated in a certain environment or in responsive to a stimulus. As such, data elements of known networks and pathways can be used as indicators of the functioning of the pathways, and a multidimensional point provides a sensitive indicator of network or pathway function. As such, perturbation of a gene that alters a biochemical network or pathway will alter the value of the multidimensional coordinate point corresponding to the network or pathway. Accordingly, the function of a gene can be assessed by determining the effect of its modulation of multidimensional shape space, which contains multidimensional coordinate points representing components of networks and pathways contained in a biochemical system.

The invention provides a method for assigning a cellular function to a component of a biochemical system. The method involves (a) determining a multidimensional shape space for at least two networks of a biochemical system in a reference state; (b) perturbing a component of a pathway within said biochemical system; (c) determining a perturbed multidimensional shape space for a network in said perturbed biochemical system, and (d) determining a multidimensional coordinate point altered between reference and perturbed multidimensional space spaces of said network, said multidimensional coordinate point corresponding to a component, the component being assigned a cellular function of said reference network.

A multidimensional coordinate point can represent data elements of a set of two or more components. For example, a multidimensional coordinate point representative of the data elements of two molecules is defined by two parameters corresponding to the data elements of the two components. Similarly, a multidimensional coordinate point representative of the data elements of three molecules is defined by three parameters corresponding to the data elements of the three components. A multidimensional coordinate point representative of the data elements of n molecules is defined by n parameters corresponding to the data elements of n molecules.

A multidimensional coordinate point can represent a single component, for example, when two or more data elements describe the component. The two or more data elements can be the same type of data elements, for example, two or more values describing expression of the component in two or more biochemical systems in the same state. The two or more data elements can be different types of data elements, for example, one mRNA expression data element and one protein expression data element. Such multidimensional coordinate points can be compared to biochemical system state-, network- or pathway-associated data element reference regions that correspond to the type of data elements contained in the particular multidimensional coordinate point. For example, a multidimensional coordinate point that represents two different types of data elements is compared to a data element region containing multidimensional coordinate points representing the same two different types of data elements. Similarly, multidimensional coordinate points representing two or more components are compared to biochemical system state-, network- or pathway-associated data element reference regions corresponding to the same set of components.

A "component multidimensional coordinate space" can be a multidimensional representation of a data element of a component of a biochemical system relative to that of other components in the system. Each dimension of the component multidimensional coordinate space can be defined by a relationship between the component and other components of the system, such as relative differences between the values of data element. Each dimension of the component multidimensional coordinate space also can represent a comparison between two or more values of a component data element relative to a standard. A comparison between component data element values can be determined without a standard, or relative to an internal standard, or relative to a reference region. For example, a component multidimensional coordinate space can contain a comparison of data elements without a standard when a value for each parameter in multidimensional space is obtained by comparing a data element value of a component to the value of that data element for each other component in the set of components where the number of components in the set=n. A component multidimensional coordinate space can contain a comparison of data elements relative to an internal standard when a value for each parameter in multidimensional space is obtained by determining the differences between the value of a component data element to that of another component data element for n components. In each of these cases, the component multidimensional coordinate space describes a single component relative to other components in a set.

Multidimensional coordinate points and spaces contain values representing component data elements. A data element can represent any factual characteristic of a biochemical system component that it represents, for example, nucleic acid expression, protein expression, polypeptide-polypeptide interaction, nucleic acid-polypeptide interaction, metabolite abundance, and growth rate.

A multidimensional shape space can be determined for a pathway, network, or biochemical system, and can contain a network- or pathway-associated reference data element region, which represents the values of data elements for components associated with a particular network or pathway. Once a network-associated reference data element region has been determined for a group of components, a sample of any biochemical system, such as from an individual, can be analyzed with respect to the data element values of the group of components. A multidimensional coordinate point can be determined that is representative of the values of data elements of a group of components and compared to the network-associated reference data element region to determine if the expression level of that molecule lies within or outside the network-associated data element expression region and is therefore outside the perturbation limits of the reference state-associated reference data element region. Furthermore, the multidimensional coordinate point can be compared with the network-associated reference data element interval to determine if the data element of that molecule or multidimensional coordinate point of a group of molecules lies within the network-associated reference data element interval or lies above or below the perturbation limits of the reference state-associated reference data element interval.

The invention provides another method for assigning a cellular function to a component of a biochemical system. The method involves (a) determining a multidimensional coordinate point representing a data element of a set of components in a biochemical network of a perturbed biochemical system; (b) comparing said multidimensional coordinate point to a network-associated reference expression region of said set of components, and (c) determining if said multidimensional coordinate point is outside of said network-associated reference expression region, wherein a multidimensional coordinate point outside of said network-associated reference expression region indicates a perturbed state of said network, said component being linked to said perturbed network and thereby being assigned a cellular function of said network.

Similarly, this method for assigning a cellular function to a component of a biochemical system can be practiced using a pathway-associated reference expression region. The method involves (a) determining a multidimensional coordinate point representing a data element of a set of components in a biochemical pathway of a perturbed biochemical system; (b) comparing said multidimensional coordinate point to a pathway-associated reference expression region of said set of components, and (c) determining if said multidimensional coordinate point is outside of said pathway-associated reference expression region, wherein a multidimensional coordinate point outside of said pathway-associated reference expression region indicates a perturbed state of said pathway, said component being linked to said perturbed pathway and thereby being assigned a cellular function of said pathway.

The methods of the invention use statistically determined component-associated data element regions, pathway-associated data element regions, network-associated data element regions, and biochemical system-associated data element regions, including reference state-associated and perturbed state-associated data element regions. The different statistically determined regions can be used in methods for assigning a function to a gene.

In one embodiment, the methods of the invention use a statistically determined network-associated data element region or pathway-associated data element region of components indicative of data element values of components in a reference population having a selected reference or perturbation state, thus accounting for natural variation in the values of data elements in a reference population. The values of data elements of components in a specimen from an animal or sample of cells, which is represented by a multidimensional coordinate point, can be compared to a statistically determined network- or pathway-associated data element region. The determination of the network- or pathway-associated data element region provides a basis for comparing any equivalent sample or specimen to determine if a biochemical system has one or more molecules with aberrant data element values. Thus, the determination of a network- or pathway-associated reference expression region for various biochemical networks in a cell provides a central repository of information, which can be accessed by a variety of means to assign a function to a gene. A network-associated reference data element region or pathway-associated reference data element region can be assigned for a set of components representative of several cellular functions of a cell type, such as a leukocyte. For example, network- and pathway-associated reference data element regions can represent normal states of cellular functions. By comparison with such network- or pathway-associated reference data element regions, it can be determined if a perturbed state of a biochemical system has normal or aberrant function of a particular network. A perturbation of a component of a biochemical system, such as a knock-out of a particular gene, can result in a shift of a multidimensional coordinate point representing a particular cellular function from a normal state to a perturbed state of the biochemical system, if the perturbation alters function of the network. As such, when network- or pathway-associated data element regions have been determined for several networks or pathways, each representing a particular cellular function, the effect of a particular perturbation of a variety of cellular functions can be readily determined. A component whose perturbation results in perturbation of a particular network or pathway from a normal or reference state is considered to be a component that functions in that network or pathway, and thereby is assigned the function of that network or pathway.

To obtain a statistical sampling of the values of data elements of molecules in a reference biochemical system, the data elements, such as expression levels, of components in a population of reference biochemical systems are determined by the methods disclosed herein, and are described as a multidimensional coordinate point. Once the multidimensional coordinate point of components in the population are determined, well known statistical analysis can be applied to provide a statistically useful network associated reference data element region. If needed, the multidimensional coordinate point of additional reference biochemical systems can be determined and added to the previously determined data elements until statistically useful reference unperturbed system regions are determined. Similarly, multiple reference unperturbed network, pathway, or biochemical system regions can be determined from multiple reference biochemical systems.

Methods of the invention, for the purpose of determining whether a component of a biochemical system is within a network-associated reference data element region or pathway-associated reference data element region can include linear, non-linear, and/or multivariate calculations from fields including mathematics, statistics, and/or computer science. Such calculations can proceed in two phases: (1) an overall computation involving training and/or estimation using data from the reference biochemical system(s) and (2) a simpler computation for a component using the results of phase 1. The end result or such calculations is to provide one or more qualitative or quantitative indicators of whether a biochemical system contains a perturbed network.

A variety of calculations can be used in the methods of the invention. Exemplary calculations useful in methods of the invention include discriminant analysis, in which a new biochemical system is classified from known calculations by training with a set of biochemical systems of known classification. For example, data from normal or perturbed biochemical systems can be used to classify a new biochemical system as having one of these known states. Other exemplary methods include classification analysis, which is similar to discriminant analysis, and multiple discriminant analysis.

Cluster analysis is a collection of methods to find groups in a set of data. Cluster analysis can be used to find groups, for example, to group network-associated molecules. Analysis of variance (ANOVA) is a general statistical technique useful for testing the significance of differences between and among groups.

Regression analysis is a general statistical analysis for predicting based on observations and can be used, for example, to predict a state of a biochemical system. Logistic regression analysis can be used for the purpose of classification. Regression trees is a predictive method based on a tree structure trained from a set of data. The data set can be based on the expression levels of molecules or combinations of molecules. Training is carried out with a series of decisions. For example, a first decision can be if a molecule or group of molecules is expressed at a high or low level. Then a decision can be based on the expression of another molecule or group of molecules, and so forth. The method is data-based and can be used for predicting the relationship between molecule expression levels and health state. Decision trees are similar to regression trees, but the emphasis is on making a decision, for example, deciding the state of a biochemical system. Nearest neighbor algorithms are distance based classification methods to assign the closest match to an individual and are useful for system-to-system comparison of complex components.

Principal components, factor analysis, multidimensional scaling and other methods of dimensionality reduction are methods to reduce the number of combinations of molecules for an effective classification. Likelihood models are methods using statistical data and probability models to provide optimal use of statistical information, where applicable. Likelihood models provide a specific description of the pattern of variation in data and can be used for estimating and hypothesis testing. Hypothesis testing is a formal process of using data to make decisions. Hypothesis testing can be used to test whether a molecule or set of molecules is useful and should be included in a group. Hypothesis testing can also be used to decide if a pool of individuals is significantly different from another pool or group of biochemical systems.

Derived variables can be created and used to increase dimensionality beyond the number of molecules in order to help a statistical method achieve an effective classification. For example, interaction terms formed by multiplying the express levels of selected pairs of molecules can be used.

Kernel density estimation and other smoothing techniques are methods used for the purpose of averaging out or eliminating noise in data or statistical variation in data. Cross-validation and other methods to guard against overfitting of the data are used in particular to protect against over optimism or over extension of data regarding the performance of a diagnostic system from a body of data. Cross-validation serves to prevent an overly optimistic appearance of the data, for example, a set of data can appear to be predictive of two distinct groups, where cross-validation can be used to compensate for an apparent overly optimistic appearance of the data. For example, if one observation is repeatedly omitted from a data set of individuals with known health states, its classification based on the remaining data can be used to obtain a more realistic indication of system performance.

Bootstrap and other statistical resampling techniques are methods used to resample from the data in order to assess the variability of the system computed from such data. Artificial intelligence, including artificial neural networks, machine learning, data mining, and boosting algorithms can also be used. Machine learning is a collection of automated methods in which training can be used to learn what distinguishes a group, for example, groups of different states of a biochemical system, and is then used to classify a biochemical system into a group. A boosting algorithm is an example of machine learning and is based on taking a simple system of classification methods to assemble more complex methods. For example, in a boosting algorithm, the expression levels of molecules taken one at a time can be analyzed in a particular sequence to generate a more effective method. Data mining is a method based on learning and inferring from large bodies of data and is useful for understanding how to use a large data set for calculations. Data mining is particularly useful when using large data sets, for example, examining a large number of sample molecules and/or a large reference population.

The methods of the invention can include a statistical calculation of the degree of confidence associated with the assignment of an individual to a health state.

Bayesian analysis using prior probability distributions is a method that uses expert opinion with prior probabilities along with observed data to make a decision. The method can therefore incorporate expert opinion to aid in decision making based on prior probability distributions.

Any one, or combination of two or more, of the statistical methods described above, or other statistical methods useful for characterizing the data elements, including multidimensional coordinate points, of components to determine whether a component data elements are altered in a perturbed biochemical system, can be used in methods of the invention.

In methods of the invention, a reference unperturbed system region indicates a reference unperturbed system state of a biochemical system, such as a cell, organ, animal or organism. A perturbed expression profile indicates a perturbed state of a biochemical system, that is, a state different from the reference population, and can indicate an abnormal or perturbed state in the biochemical system. The methods of the invention can therefore be used to determine if a biochemical system is perturbed, even though an animal has no signs or symptoms indicative of perturbation.

As used herein, a "reference biochemical system" or "reference individual" refers to a biochemical system, which can be an individual, that is selected for comparison using defined criteria. One skilled in the art can readily determine criteria suitable for inclusion of an individual as a reference individual for a particular application of methods of the invention, as described below. As used herein, a "reference population" refers to a group of two or more reference individuals.

Any relevant criteria can be used for identifying a suitable reference biochemical system for a desired comparison. For example, a reference biochemical system can be a normal biochemical system that is essentially unperturbed. Once reference criteria have been identified, for example, the reference criteria of being an unperturbed biochemical system, a population of biochemical systems, such as cells, organs, organisms, or individuals, is selected as reference biochemical systems to determine an unperturbed or reference-associated reference region of components of the biochemical system. One skilled in the art can readily determine desired criteria for the reference population and select biochemical systems fitting the desired criteria. In one embodiment, the reference population is an unperturbed biochemical system, or subsystem, such as a network or pathway. For example, due to genetic variation, unperturbed individuals will express variable levels of a given gene depending on the genotype of each individual. These variable expression levels of a given gene in a population of individuals correspond to a range of expression levels characteristic of the unperturbed state of the individuals. Such an expression range can be predetermined by sampling a sufficient number of reference individuals and determining the corresponding statistically useful unperturbed or reference state-associated reference expression regions found in these individuals.

A network contains a set of components linked by at least two data elements, at least one of the data elements represented by a multidimensional coordinate point, each component having an interaction, interrelation or interdependence on another component. One or more networks can be described by an integrated multidimensional data space. An integrated multidimensional data space is determined by identifying a set of components linked by at least two data elements, at least one of the data elements represented by a multidimensional coordinate point. Components of a biochemical system can be linked by a variety of types of data elements. Linkage between components of a system can be determined with or without knowledge of changes that occur in response to a system perturbation. For example, physical interactions between a group of components can be determined for an unperturbed system, a perturbed system, or can represent the changes between unperturbed and perturbed states of the system. Linkage between components by an expression data element is identified when expression elements of components are changed, either increased or decreased with respect to each other, when the biochemical system is perturbed.

Therefore, an integrated multidimensional data space can include merging one set of data elements representing a system in a reference state with another set of data elements representing that system in a reference state, perturbed state, or difference between a reference and perturbed state. For example, an integrated multidimensional data space can include a network of genes linked together by known physical interactions between their encoded protein products, and by multidimensional coordinate points representing the changes in gene expression that result from a specific perturbation.

To determine components included in an integrated multidimensional data space, a set of data elements, for example, a set of multidimensional coordinate points representing expression data elements of a biochemical system in a reference state, can be constrained by a set of second data elements, for example, a set of physical interaction data elements representing direct interactions between a group of components.

The types of data elements selected for producing a multidimensional data space will depend on the types of measurements are feasible for a particular system. The selected component characteristics incorporated into a integrated multidimensional data space will produce a integrated multidimensional data space that can be used to assign a function to a gene based on the selected characteristics. However, any particular characteristics can be selected because a change in a multidimensional coordinate point, regardless of the types of data elements it represents, can indicate that one or more components represented by the multidimensional coordinate point function in a particular pathway or network.

The methods of the invention for identifying components of a biochemical network and for assigning a cellular function to a gene involve comparing two or more multidimensional shape spaces or integrated multidimensional data spaces. Two or more multidimensional shape spaces or integrated multidimensional data spaces can be compared by determining the differences between multidimensional coordinate points that describe characteristics of each component represented in a multidimensional shape space or integrated multidimensional data space. The methods used for determining such differences will depend upon the complexity of the multidimensional coordinate points of the multidimensional spaces.

Comparing two or more multidimensional coordinate points involves determining correlative changes between components of a biochemical system under two or more different conditions. Alterations in data elements that correspond to a particular condition of a biochemical system can be detected by comparing values representing data elements, including multidimensional coordinate points, of system components under the different conditions. Therefore, multidimensional shape space describes correlative changes among data elements of components of a biochemical system, and thus describes the interactions, interrelations and interdependencies of system components contained in networks and pathways because correlative changes reveal components that regulate characteristics of each other, or are co-regulated by a common component. For example, a perturbation of a single component of a biochemical system can result in alterations of one or more characteristics of system components that interact with, are regulated by, or whose regulation is affected by the perturbed component. These relationships between components are evidenced by both jointly coordinated and inversely coordinated changes in component characteristics reflected in multidimensional coordinate points within multidimensional shape spaces.

The invention provides a method for assigning a function to a gene by comparing multidimensional shape spaces. The method involves (a) determining an integrated multidimensional data space for each of at least two networks in a reference state biochemical system; (b) determining a multidimensional shape space for at least one network in a perturbed state biochemical system, and (c) determining a component multidimensional coordinate point contained within a multidimensional shape space representing the difference between multidimensional data spaces of reference and perturbed states of said biochemical system, said component being linked to said network having perturbed multidimensional shape space, and thereby being assigned the cellular function of said network.

The invention provides another method for assigning a function to a gene by comparing multidimensional shape spaces. The method involves (a) comparing two integrated multidimensional data spaces of a biochemical system obtained in reference and perturbed states of a biochemical system, said integrated multidimensional data spaces comprising at least two networks, and (b) determining a component multidimensional coordinate point contained within a multidimensional data space representing the difference between multidimensional data spaces of reference and perturbed states of said biochemical system, said component being linked to said network having said perturbed multidimensional shape space, and thereby being assigned a cellular function of said network.

To determine the function of an uncharacterized gene, the functions of components contained in the multidimensional data spaces of the reference and perturbed biochemical systems can be known or unknown. When a component having a known cellular function within a pathway is determined to have a multidimensional coordinate point altered in a perturbed biochemical system, the cellular function is assigned to the uncharacterized gene. When a component having an unknown cellular function is determined to have a multidimensional coordinate point altered in a perturbed biochemical system, either a different component that does have a determined cellular function and also is determined to have a multidimensional coordinate point altered in a perturbed biochemical system can be used to assign a cellular function to the uncharacterized component, or one or more additional perturbations to the biochemical system can be performed until a component having a known cellular function is determined to have a multidimensional coordinate point altered in the perturbed biochemical system.

A difference between two multidimensional coordinate points, for example, those representing nucleic acid or polypeptide expression data elements, can be determined by calculating a mathematical difference in absolute or relative numerical values representing the multidimensional coordinate points. Such determinations generally are performed using a computer program or machine capable of calculating, identifying or listing differences in multidimensional coordinate points of two or more multidimensional shape spaces or integrated multidimensional data spaces.

Comparisons between two or more multidimensional shape spaces or integrated multidimensional data spaces can involve comparing multidimensional coordinate points representing data elements of substantially every component of a multidimensional shape spaces or integrated multidimensional data spaces, a subset of components, components of one or more specific networks or pathways, as well as many, several or a few components from common or different pathways or networks.

The comparison of two or more multidimensional data spaces, including, integrated multidimensional data spaces can include comparing correlative changes among one or more selected data elements of one or more components of a biochemical system under two or more different conditions, at least one of the data elements represented by a multidimensional coordinate point. For example, correlative changes in a single component, a few components, many components or substantially all of the components of a biochemical system can be compared between two or more conditions of a system. Any number of components can be represented by a multidimensional coordinate point. Correlative changes can be identified for components in any pathway or network described by in a multidimensional data space. Therefore, correlative changes of components from a single pathway or network, more than one pathway or network, at least two pathways or networks, at least three pathways or networks, at least four pathways or networks, at least five pathways or networks, or substantially all pathways or networks described by a multidimensional data space can be determined in order to assign a function to a gene or identify a component of a biochemical network. Comparisons can similarly be made between two or more different biochemical systems.

A comparison of multidimensional data spaces, including integrated multidimensional data spaces, obtained from for a biochemical system under two different conditions, such as reference and perturbed biochemical systems, can be used to describe the differences or changes in the biochemical system under a perturbed condition. A perturbation to a biochemical pathway can result in changes within a pathway component, changes in a network containing the pathway and changes in another network. A perturbed biochemical system contains at least one component having an altered characteristic compared to the unperturbed system.

The methods of the invention are applicable to determining components of a network and determining the function of a gene within large and small biochemical systems, so long as a multidimensional coordinate point can be determined for a set of components in the biochemical system. A system includes a collection of individual components that work together as a unit. Whether the working unit is referred to, for example, as a system, subsystem, network, pathway, set or group of components, is unimportant to practice the methods of the invention so long as the methods are applied to a system that functions as a unit. Thus, the methods of the invention can be used to determine pathway components, system components, network components, or to determine the function of a gene in both simple and complex systems as well as in multiple systems.

The methods of the invention for assigning a cellular function to a gene can be practiced using a variety of biochemical systems, including a mammal. Although a particular perturbation in a mammal can primarily affect one or a few physiological systems, for example, perturbation of a gene involved in regulating cardiovascular function affecting primarily the cardiovascular system, it is expected that a relatively homogeneous population of cells can provide a representative sampling of cells reflective of a variety of physiological systems, even if those cells are not directly associated with the particular perturbation. One such relatively homogeneous population of cells representative of a variety of physiological systems is white blood cells (WBCs), or subpopulations thereof. Accordingly, the methods of the invention can be conveniently performed with a specimen from an mammal such as WBCs, which are readily accessible and can provide a window into many physiological systems, including cardiovascular, nervous, immune, gastrointestinal, endocrine, hepatic, lymphatic, neuromuscular, renal, respiratory, skeletal, and urogenital, metabolic systems, and the like, as disclosed herein.

For example, although a particular perturbation can affect primarily cells of the renal system, it is expected that WBCs, which may not be directly involved in the renal perturbation, will nevertheless provide a window for observing physiological changes associated with the renal perturbation. The use of WBCs to monitor a variety of physiological changes is advantageous in that it obviates the need to obtain tissue specimens directly affected by the perturbation. Instead, readily accessible WBCs are used.

In addition, macrophages, a subpopulation of white blood cells, respond to physiological changes, which in turn results in biochemical changes in the macrophages. Accordingly, macrophages can function as a window into the physiological changes that occur when a mammal has undergone a perturbation. Therefore, macrophages, or other WBCs or subpopulations thereof, provide a window into observing the physiological changes that occur at the cellular level of changes in biochemical network and pathway function that can occur in a mammal perturbed by a physical, chemical, environmental or genetic change.

Furthermore, the relatively homogeneous population of WBCs can be further fractionated, for example, into lymphocytes such as T cells or B cells, granuolocytes, monocytes, macrophages, neutrophils, eosinophils, basophils, mast cells, and the like, and still be used as a representative sampling of cells useful for monitoring a variety of physiological systems. Even a single cell can be used as a representative specimen from a mammal for use in methods of the invention.

An index, a classification, an automatic selector, or any other system of information retrieval can be used as a tool to organize and obtain information in multidimensional data space. The methods of the invention for determining components of a pathway or network or determining the function of a gene can involve assimilating individual component characteristics into an organized representation. A multidimensional shape space, including an integrated multidimensional data space, can be represented in a variety of formats, including, for example, as raw data values, mathematical transformations of raw values, a set or summary of raw or transformations of raw values, tabular, chart, and graphical forms, including three-dimensional representations. A variety of visual representations can be used to represent the data elements of components of a biochemical system or network. Color hue and intensity, line thickness, depiction or three-dimensionality, geometric shape and size are examples of readily recognized visual parameters. A multidimensional shape space can therefore be described by an output representation, such as a chart, graph, or three-dimensional representation. An output representation can be prepared by processing raw or transformed data values manually or by computer, using a variety of algorithms well known in the art.

The methods of the invention can include the step of comparing data elements of components in a biochemical system or a multidimensional coordinate point representing data elements of two or more components, with a network-associated reference data element region or pathway-associated reference data element region. Although not required, the network- or pathway-associated reference data element region for the components is generally determined prior to determining the data elements of components in a biochemical system from a perturbed state of the biochemical system. Furthermore, it is possible that the data elements that define a multidimensional coordinate point for two or more components in the system is determined at a different time than the determination of the data elements that define a second multidimensional coordinate point in a sample. Whether the data elements of a component are determined simultaneously with the determination of data elements for a second component in a sample or the determination of a network- or pathway-associated reference data element region of the components, it is understood that such determinations are made under conditions that allow a statistically useful comparison, even if obtained at different times.

The methods of the invention can be used in a multiparameter analysis by measuring a data element, such as an expression level, of multiple components within a biochemical system. The components can be representative or a particular network or pathway. Multiple components representative of a network or pathway are those components having data elements that correlate with a state of a network or pathway. A state of a network can be, for example, a reference state, such as a normal state of a cell, in which network components have an expected amount of activity, expression, physical association, or other characteristic described by a data element. A network also can be in a perturbed state, such as when a biochemical system is subjected to a chemical, environmental or genetic change. In such a perturbed state, network components also have an expected amount of activity, expression, physical association or other characteristic described by a data element. Because the state of a network or pathway reflects the state of a biochemical system, a data element region representative of a state of a network or pathway can be used as a system-associated biochemical data element region.

A multidimensional coordinate point that describes data elements of several network components, for example, expression of several components of a network, can be compared to a network-associated reference data element region representing the expression changes of the individual components determined for the same several components in a reference biochemical system. Such a comparison is useful for determining whether a perturbation in a biochemical system results in perturbation of one or more particular biochemical network. The ability to determine whether a biochemical network is in a reference or perturbed state can be used to determine whether knock-out, over-expression or otherwise altering the function of a particular gene causes perturbation of a network assigned to a cellular function. The same concept applies to pathways within networks because pathway-associated data element regions can be determined for components represented by a multidimensional coordinate point and contained within a pathway.

One useful method to allow comparison between different samples containing biochemical systems is to include an internal control that can be used to normalize the values of data elements between samples. A particularly useful internal control can be, for example, a component in the sample for which the expression level does not significantly vary between a reference state and a perturbed state of the biochemical system. An internal control component can be a molecule corresponding to or encoding molecules such as actin, other cytoskeletal proteins, or any polypeptide or encoding nucleic acid that does not significantly vary between reference and perturbed states of the biochemical system. Alternatively or in addition, an exogenous control molecule can be added to normalize variability between samples collected at different times or from different individuals.

The use of internal and exogenous controls also allows determination of the reproducibility of sample collection and analysis. One skilled in the art will know or can readily determine if a data element determined for a component, such as a component in a reference biochemical system and useful for obtaining a network- or pathway-associated reference data element region, is reproducible and reliable for use in methods of the invention based on statistical analysis and determination of experimental variability.

A perturbation state of a biochemical network is a condition of a biochemical system in which one or more network components have a characteristic, such as a level of expression or activity, that is altered from the level of expression or activity of the component in the unperturbed state of the biochemical system. A cell or organism containing a perturbation state of a biochemical network can be generated experimentally or obtained from a natural source. A perturbation state of a biochemical network can be generated using a variety of experimental methods, such as, for example, genetic and environmental perturbations, as described above. Therefore, cells or organisms having gene deletions or altered expression levels of a network component, and cells or organisms subjected to an environmental change such as treatment with a drug, contain a biochemical network having a perturbation state.

A perturbation state of a biochemical system can also be caused by or result from a disease or other abnormal state of an organism, including genetic abnormalities. Therefore, a cell or organism containing a either a naturally occurring or induced perturbation state of a biochemical system is applicable to the methods of the invention.

A perturbation of a biochemical system includes any type of condition that alters a characteristic of a biochemical system component. A perturbation can be applied to any type of component of a biochemical system, such as, for example, a gene, polypeptide, macromolecules and organic and inorganic molecules. Thus, a perturbation to a biochemical system can be applied, for example, by altering or perturbing a characteristic of a component of a biochemical system. A characteristics of a component can be perturbed directly, indirectly, or both. A direct perturbation is an alteration of a component that is independent of the characteristics of other system components. A direct perturbation of a system component includes a genetic manipulation that specifically alters a property of the component, such as expression, activity or physical interaction. For example, the expression of a component can be altered by gene overexpression, deletion or mutation, and by mutation of a gene that positively or negatively regulates component gene expression.

The activity of a component can be altered, for example, by mutation of the component gene that results in a component polypeptide having altered activity. Gene mutations include, for example, nucleotide substitutions, deletions, truncations, and fusions with heterologous nucleic acids. Altered activity can be an increase or decrease in functional activity, a change in conformation that alters function or binding to another molecule, or a change that results in altered modification, such as increased or decreased phosphorylation, glycosylation, or other polypeptide modification. A direct perturbation can include a change in any system component characteristic represented by a data element.

An indirect perturbation of a system component can be a change in the cellular environment containing the system component that results in a change in a characteristic of the component, such as, for example, expression, activity or physical interaction. An indirect perturbation of a component can be, for example, an environmental manipulation of an organism or cell that alters a characteristic of a system component. For example, changes in temperature, nutrition, introduction or withdrawal of certain factors from growth medium, and treatment with drugs can be used to alter a characteristic of a component. An indirect perturbation can be used to alter a system component characteristic represented by a data element.

A perturbed biochemical system can contain multiple perturbations. For example, perturbations can be made to components contained within distinct networks or to more than one component in a particular network, including substantially all of the components of a network or pathway. In addition, a combination of direct and indirect perturbation of one or more components of a biochemical system can be performed. For example, a direct perturbation such an alteration of a component that results in a change in component expression, activity, or physical interactions can be combined with an indirect perturbation such as an environmental perturbation that initiates the biochemical function of the perturbed component. A specific example of a combination of direct and indirect perturbations useful in the methods for predicting the behavior of a biochemical system and identifying a functionally interactive components of a biochemical network is the deletion of a component gene involved in a extracellular ligand stimulated signaling cascade pathway, combined with the indirect environmental perturbation of ligand addition to the biochemical system to initiate the signaling cascade pathway. Thus, a perturbed biochemical system can have one, two, three, four, five, six, seven, eight, nine, ten or more perturbations.

Due to the sequential relationship among pathway component disruption or alteration of one component of a pathway alters the biological function of the pathway. An alteration in the biological function of a pathway can be manifested in a variety of ways, depending on the particular perturbation and function of the pathway. For example, the function of a biochemical pathway can be enhanced, inhibited, terminated at a particular step or stage or can affect a different outcome from a normal function, in response to a perturbation of a pathway component.

A perturbed biochemical pathway can also affect the biochemical function of a biochemical network containing the perturbed pathway. For example, a biochemical pathway can result in the production of a product that initiates the biochemical function of another biochemical pathway. Lack of production of such a product, such as through a perturbation of a biochemical pathway, would therefore alter the biochemical function of the second pathway which would be initiated under unperturbed conditions. Therefore, components of a biochemical system that are altered in response to a perturbation of a biochemical pathway component are contained within the biochemical network of the perturbed pathway.

A biochemical pathway component selected for perturbation can be known or suspected to be involved in a specific biochemical pathway, or can have an unknown function. When applying the methods for determining the function of an uncharacterized gene or gene having an unknown function, it can be useful to perturb that gene, and determine the effect of the perturbation on multidimensional space of a pathway, network or biochemical system. Due to the interactions, interrelations and interdependencies of components of a biochemical system, perturbation of a single component will effect other components within the pathway or pathways in which the component functions. Such effects on pathway components also will be reflected in a network containing the pathway. Therefore, either pathway, network or biochemical system multidimensional space will contain changes in multidimensional coordinate points representing components that function in concert with the perturbed component.

When applying the methods for determining the function of a gene, it is useful to perturb a component known to function in a particular pathway because such a perturbation of a pathway component will result in changes to other components of the pathway. For example, a biochemical pathway can include an enzymatic pathway that results in conversion of one compound to another. A response of a component of such a biochemical pathway can be, for example, production of the product compound or an enzymatic activity. Another example of a biochemical pathway is a gene expression pathway. A response of a component of a gene expression pathway can be, for example, expression or lack of expression of a particular gene. A further example of a biochemical pathway is a regulatory pathway. A response of a component of a regulatory pathway can be, for example, enzymatic activity, metabolite or product production, gene expression or any other characteristic of a component of the perturbed biochemical system that reflects the biochemical function of the regulatory pathway.

Those skilled in the art will know or can determine methods for measuring a response to a pathway component perturbation in a particular biochemical system. Such a response can be measured, for example, relative to a reference condition of a biochemical system, such as an unperturbed state of the system. Those skilled in the art will be able to determine a response of a pathway component that will reflect the biochemical function of the pathway, such that, for example, a disruption of a biochemical pathway can be detected.

The methods of the invention for perturbing a characteristic of at least one pathway component can also be applied to at least two, three, four, five, or more pathway components. Any number of pathway components can be perturbed in order to assign a function to a gene or identify a component in a biological network. For example, a single component, a few, many or every component known to participate in a particular pathway, network, or biochemical system, can be subjected to perturbation, if desired. The methods of the invention for assigning a function to a gene or identifying components of a network can include perturbing more than one component of a biochemical pathway because each perturbation can lead to the identification of additional components of a biochemical pathway network. When it is desired to identify all components of a biochemical network or pathway, for example, perturbation of all known components of a biochemical pathway is advantageous. Components of a biochemical pathway can be perturbed individually, or more than one pathway component can be perturbed to produce a perturbed biochemical system.

Therefore, the invention provides a method for identifying functionally interactive components of a biochemical network. The method involves (a) determining a set of components of a biochemical system, each component linked to another by a common first data element; (b) determining a set of components of a biochemical system linked by a common second data element, the second data element represented by a multidimensional coordinate point corresponding to each component, and (c) integrating the set of components linked by a common first data element with the set of components linked by a common second data element represented by a multidimensional coordinate point corresponding to each component, to produce a network of functionally interactive components, each component within said network of functionally interactive components being characterized as linked by at least two data elements.

The methods of the invention for identifying interactive components of a biochemical system are useful for identifying a network of components. The components of a network can include the components contained in a biochemical network or pathway. Thus, the methods for identifying functionally interactive components can be used, for example, to identify components of a biochemical pathway or network. A component of a network has at least two characteristics in common with another component. The common characteristics can be, for example, levels of expression or activity of a component, physical interaction, and characteristics of a biochemical system containing the component under a specified condition. Common characteristics of components of a network can be determined by identifying correlative changes between components under two or more different conditions of a biochemical system. A component that is functionally interactive within the system is a component that has at least two characteristics in common with another component of a network, at least one characteristic of each component being represented by a multidimensional coordinate point.

The methods of the invention for identifying a functionally interactive component of a biochemical system involve obtaining a set of components within a biochemical system linked by at least two component characteristics, one of the component characteristics represented by a multidimensional coordinate point. The components contained in a set of components linked by a component characteristic each have a characteristic represented by a data element that is shared or that undergoes a mutual or reciprocal change under a common specified condition of a biochemical system. Components can be linked, for example, by physical interaction, expression, activity, phenotypic change and metabolite abundance.

A set of components linked by physical interaction contains components that each have at least one physical interaction with another component of the set. A set of components linked by expression or activity each have altered expression or activity under a specified condition of a biochemical system. For example, a set of components linked by expression or activity can be obtained by perturbing a biochemical system, determining changes in expression or activity, and identifying a set of components that underwent a change correlating with the perturbation. Such a change can be reflected in an altered multidimensional coordinate point that represents a change in expression or activity of at least one component represented by the multidimensional coordinate point.

The methods of the invention for identifying functionally interactive components of a biochemical system involve integrating a set of components linked by two or more common characteristics. A specific example is the integration of a set of physically linked components with a set of components linked by expression or activity, and described by at least one multidimensional coordinate point. In a specific example, the method involves identifying all of the physical interactions known for a particular biochemical system, determining changes in multidimensional shape space corresponding to multidimensional coordinate points describing expression or activity of the components of the biochemical system under two or more different conditions, and retaining components that have both a physical interaction with another system component and an alteration in expression or activity represented by a multidimensional coordinate point under a specified condition of a biochemical system.

The method also can be practiced by determining a set of system components that are different or undergo a change between two or more different conditions of a biochemical system by comparing multidimensional shape spaces under two or more different conditions of the biochemical system, and then determining which of those components physically interact with another component of the subset of the biochemical system that has altered expression or activity under a specified condition of a biochemical system. Similarly, other characteristics of a biochemical system or system component can be integrated to identify components of a network.

The invention provides a method for identifying a component of a biochemical network. The method involves (a) determining an integrated multidimensional data space for a biochemical system comprising at least two networks; (b) perturbing at least one component of a biochemical pathway, and (c) determining a multidimensional coordinate point for a candidate network component affected by said perturbing of the biochemical system, wherein a candidate component having an altered multidimensional coordinate point in response to said perturbation is identified as a component of said biochemical network.

The methods for identifying a component of a biochemical network can be applied to identifying network components de novo, or to identifying system components to be added to a biochemical network having two or more components.

Candidate components of a biochemical network can be determined by identifying components that have a characteristic in common with a pathway component. For example, a system component that has an interaction with a pathway component is a candidate component of the network. A group of candidate components can therefore be determined by identifying system components that interact with pathway components. The components of a pathway function in a sequential manner such that affecting one component of a pathway, such as by perturbing the component, can affect a response of other components in the pathway. Similarly, perturbation of a pathway component can affect the response of a component in the network containing the pathway. Therefore, a candidate network component exhibiting an altered characteristic as a result of a pathway perturbation, such as a change in expression or activity, is identified as a component of the biochemical network.

The invention provides a method for identifying a compound that restores a biochemical system to a reference state. The method involves (a) determining an integrated multidimensional data space for a reference state of a biochemical system; (b) determining an integrated multidimensional data space for a perturbation state of a biochemical system; (c) contacting a biochemical system exhibiting the perturbation state with a test compound; (d) determining a multidimensional shape space for said biochemical system contacted with said test compound, and (e) identifying a compound that restores at least two multidimensional coordinate points in said perturbed multidimensional data space to reference state conditions, said compound having the ability to restore a biochemical system to a reference state.

The methods of the invention for identifying a compound that restores a biochemical system to a reference state involve comparing two or more integrated multidimensional data spaces or comparing a multidimensional data space to a multidimensional shape space. Such comparisons are described herein, in reference to the methods of identifying components of a network and identifying the function of a gene. Comparisons between integrated multidimensional data spaces and multidimensional shape spaces involve comparing multidimensional coordinate points representing data elements, or a subset of data elements, for each component of a biochemical or constituent system. Two or more integrated multidimensional data spaces having differences between 10% or fewer data elements are integrated multidimensional data spaces which are substantially the same. Similarly, a multidimensional shape space having a difference with a integrated multidimensional data space of 10% or fewer data elements is a multidimensional shape space. Alternatively, a multidimensional shape space having a difference with another multidimensional shape space, including an integrated multidimensional data space, can be determined to be significantly different based on a statistical measure, such as a p value with respect to an appropriate statistical model.

The methods of the invention for screening for compounds that restore a perturbation state of a biochemical system involve obtaining a data integration map of a perturbed biochemical system. Obtaining a data integration map is described above in reference to the methods of producing a data integration map. A data integration map describes the state of a biochemical system in terms of the interactions, interconnections and interdependencies of system components. Thus a comparison between data integration maps can reveal changes in data elements of one or more pathways and networks present in a perturbed system. A data integration map obtained from a perturbed biochemical system can have one or more altered data elements compared to a reference data integration map obtained, for example, from a corresponding unperturbed system. The effect of a test compound on at least two networks of a perturbed biochemical system can be readily observed by comparing a data integration map from a perturbed sample in the presence and absence of the test compound. The effect of a test compound on components can be observed in a multi-network level, the method thereby providing an advantage over conventional screening methods that typically measure the effect of a compound on a single component or pathway. An additional advantage provided by the methods of the invention, as applied to screening test compounds, is that test compounds can be selected based on the network components observed to be affected in the perturbation state of a sample compared to an unperturbed sample. For example, test compounds suspected or known to modulate a particular cellular function can be administered to a system having a perturbation of the corresponding biochemical network.

The methods of the invention for screening for compounds that restore a perturbation state of a biochemical system involve contacting a biochemical system exhibiting a perturbation state with a test compound. A test compound can be any substance, molecule, compound, mixture of molecules or compounds, or any other composition which is suspected of being capable of restoring a perturbation state of a biochemical system. A test compounds can be a macromolecule, such as biological polymer, including polypeptides, polysaccharides and nucleic acids. Sources of test compounds which can be screened for restoring a perturbation state of a biochemical system, for example, libraries of small molecules, peptides, polypeptides, RNA and DNA.

Additionally, test compounds can be preselected based on a variety of criteria. For example, suitable test compounds having known modulating activity on a pathway suspected to be involved in a perturbation state of a biochemical system, as determined using the methods described herein, can be selected for testing in the screening methods. For a biochemical system that has been determined to contain components that participate in more than one pathway, test compounds suspected or known to modulate each pathway can be examined for the ability to restore a perturbation state of a biochemical system using the screening methods of the invention. Alternatively, the test compounds can be selected randomly and tested by the screening methods of the present invention. Test compounds can be administered to the reaction system at a single concentration or, alternatively, at a range of concentrations from about 1 nM to 1 mM.

The method of screening for compounds that restore a biochemical system to a reference state can involve groups or libraries of compounds. Methods for preparing large libraries of compounds, including simple or complex organic molecules, carbohydrates, peptides, peptidomimetics, polypeptides, nucleic acids, antibodies, and the like, are well known in the art. Libraries containing large numbers of natural and synthetic compounds can be obtained from commercial sources.

The number of different test compounds examined using the methods of the invention will depend on the application of the method. It is generally understood that the larger the number of candidate compounds, the greater the likelihood of identifying a compound having the desired activity in a screening assay. The methods can be performed in a single or multiple sample format. Large numbers of compounds can be processed in a high-throughput format which can be automated or semi-automated.

A reaction system for identifying a compound that can restore a biochemical system to a reference state contains a mixture of the components of a biochemical system that can be modulated by a test compound. For example, a test compound can be administered to an organism, intact cell or cell preparation in which two or more network component alterations in expression or activity can be modulated by the test compound. The modulation of a biochemical system network by a test compound can be determined by determining a change in a data element represented by a multidimensional coordinate point.

A compound that restores a biochemical system to a reference state changes at least one multidimensional coordinate point in an integrated multidimensional data space of a perturbed biochemical system to a reference value. Changes in multidimensional coordinate points can be determined using a method appropriate for the mathematical complexity of the multidimensional point. A test compound that restores a multidimensional coordinate point of a perturbed biochemical system to at least about 50% of the reference value is considered to be a compound that restores a biochemical system to a reference state.

To produce an integrated multidimensional data space, a biochemical system is contacted with the test compound under conditions in which the biochemical system can respond to the compound. A biochemical system treated with a test compound can then be subjected to analytical methods for detecting a change in one or more selected data elements. Prior to analysis, the biochemical system can be processed in a manner appropriate for the method of detection.

A control reference sample can be a single sample or a pool of reference samples. For example, a control reference sample can be a pool of two or more samples of reference cells, tissues, organs, organisms, or subcellular systems used to establish an unperturbed reference sample, if desired. Such a pool of all reference systems is expected to result in a reference level that is essentially an average of the reference systems. One skilled in the art can readily determine a desired number of one or more reference individuals, including all reference systems, to include in a pool for use as a control reference system. The amount of a pooled sample is adjusted accordingly to allow direct comparison to the perturbation state test sample, for example, based on cell number, amount of protein, or some other appropriate measure of the relative amount of control reference sample and test sample.

The methods of the invention for producing a multidimensional shape space or multidimensional data space can involve determining physical interactions between system components. Physical interactions between two or more components can be demonstrated using a variety of experimental methods well known in the art, such as, for example, the yeast two-hybrid system, phage display, co-immunoprecipitation, co-purification, and co-sedimentation, and gel-shift assays. Physical interactions between system components can also be obtained by searching the literature and public or private data bases. For example, the Database of Interacting Proteins, available at the UCLA web site, is a compilation of experimentally determined yeast protein interactions (Xenarios, I. et al. Nucleic Acids Red. 28, 2890-291 (2000)). Those skilled in the art will know how to do a manual or computer-assisted search of the literature or a data base to identify reported physical interactions between system components. Similarly, those skilled in the art will know how to perform experiments most appropriate for the organism or cell under study to identify polypeptides, nucleic acids, or other molecules that interact with a pathway component.

The methods of the invention can be used to assign cellular functions to genes in an animal, including a mammal. A variety of transgenic methods can be used to perturb a component of a pathway or network in an animal. For example, transgenic methods can be used to increase, decrease, alter, or abolish expression of a gene in a mammal.

Any of a variety of techniques known in the art can be used to introduce a transgene into animals to produce the founder lines of transgenic animals, for example to increase, decrease or alter expression of a gene (see, for example, Hogan et al., supra, 1986; Hogan et al., Manipulating the Mouse Embryo: A Laboratory Manual, second ed., Cold Spring Harbor Laboratory (1994), U.S. Pat. Nos. 5,602,299; 5,175,384; 6,066,778; and 6,037,521). Such techniques include, but are not limited to, pronuclear microinjection (U.S. Pat. No. 4,873,191); retrovirus mediated gene transfer into germ lines (Van der Putten et al., Proc. Natl. Acad. Sci. USA 82:6148-6152 (1985)); gene targeting in embryonic stem cells (Thompson et al., Cell 56:313-321 (1989)); electroporation of embryos (Lo, Mol Cell. Biol. 3:1803-1814 (1983)); and sperm-mediated gene transfer (Lavitrano et al., Cell 57:717-723 (1989)).

For example, embryonal cells at various developmental stages can be used to introduce transgenes for the production of transgenic animals. Different methods are used depending on the stage of development of the embryonal cell. The zygote is a good target for micro-injection, and methods of microinjecting zygotes are well known (see U.S. Pat. No. 4,873,191). In the mouse, the male pronucleus reaches the size of approximately 20 micrometers in diameter which allows reproducible injection of 1-2 picoliters (pl) of DNA solution. The use of zygotes as a target for gene transfer has a major advantage in that in most cases the injected DNA will be incorporated into the host genome before the first cleavage (Brinster, et al. Proc. Natl. Acad. Sci. USA 82:4438-4442 (1985)). As a consequence, all cells of the transgenic non-human animal will carry the incorporated transgene. This will in general also be reflected in the efficient transmission of the transgene to offspring of the founder since 50% of the germ cells will harbor the transgene.

Transgenic animals can also be generated by introduction of the targeting vectors into embryonal stem (ES) cells. ES cells are obtained by culturing pre-implantation embryos in vitro under appropriate conditions (Evans et al., Nature 292:154-156 (1981); Bradley et al., Nature 309:255-258 (1984); Gossler et al., Proc. Natl. Acad. Sci. USA 83:9065-9069 (1986); and Robertson et al., Nature 322:445-448 (1986)). Transgenes can be efficiently introduced into the ES cells by DNA transfection using a variety of methods known in the art including electroporation, calcium phosphate co-precipitation, protoplast or spheroplast fusion, lipofection and DEAE-dextran-mediated transfection. Transgenes can also be introduced into ES cells by retrovirus-mediated transduction or by micro-injection. Such transfected ES cells can thereafter colonize an embryo following their introduction into the blastocoel of a blastocyst-stage embryo and contribute to the germ line of the resulting chimeric animal (reviewed in Jaenisch, Science 240:1468-1474 (1988)). Prior to the introduction of transfected ES cells into the blastocoel, the transfected ES cells can be subjected to various selection protocols to enrich for ES cells that have integrated the transgene if the transgene provides a means for such selection. Alternatively, PCR can be used to screen for ES cells that have integrated the transgene. This technique obviates the need for growth of the transfected ES cells under appropriate selective conditions prior to transfer into the blastocoel.

In addition, retroviral infection can also be used to introduce transgenes into a non-human animal. The developing non-human embryo can be cultured in vitro to the blastocyst stage. During this time, the blastomeres can be targets for retroviral infection (Janenich, Proc. Natl. Acad. Sci. USA 73:1260-1264 (1976)). Efficient infection of the blastomeres is obtained by enzymatic treatment to remove the zona pellucida (Hogan et al., supra, 1986). The viral vector system used to introduce the transgene is typically a replication-defective retrovirus carrying the transgene (Jahner et al., Proc. Natl. Acad Sci. USA 82:6927-6931 (1985); Van der Putten, et al. Proc. Natl. Acad. Sci. USA 82:6148-6152 (1985)). Transfection is easily and efficiently obtained by culturing the blastomeres on a monolayer of virus-producing cells (Van der Putten, supra, 1985; Stewart et al., EMBO J. 6:383-388 (1987)). Alternatively, infection can be performed at a later stage. Virus or virus-producing cells can be injected into the blastocoele (Jahner D. et al., Nature 298:623-628 (1982). Most of the founders will be mosaic for the transgene since incorporation occurs only in a subset of cells which form the transgenic animal. Further, the founder can contain various retroviral insertions of the transgene at different positions in the genome, which generally will segregate in the offspring. In addition, it is also possible to introduce transgenes into the germline by intrauterine retroviral infection of the midgestation embryo (Jahner et al., supra, 1982). Additional means of using retroviruses or retroviral vectors to create transgenic animals known to the art involves the microinjection of retroviral particles or mitomycin C-treated cells producing retrovirus into the perivitelline space of fertilized eggs or early embryos (WO 90/08832 (1990); Haskell and Bowen, Mol. Reprod. Dev. 40:386 (1995)).

The methods of the invention for identifying components of a biochemical network and identifying the function of a gene involve measuring a characteristic of a biochemical system, constituent system or system component. One characteristic that can be conveniently measured is gene expression level of a biochemical system component. A change in gene expression can be measured, for example, by detecting the amount of mRNA encoded by a gene or the amount of polypeptide corresponding to a given amino acid sequence encoded by a gene.

The methods of the invention involve measuring changes in gene expression by detecting the amount of mRNA or polypeptide present in a sample. Methods for measuring both mRNA and polypeptide quantity are well known in the art. The methods for measuring mRNA typically involve detecting nucleic acid molecules by specific hybridization with a complementary probe in solution or solid phase formats. Such methods include northern blots, polymerase chain reaction after reverse transcription of RNA (RT-PCR), and nuclease protection. Measurement of a response of a pathway component can be performed using global gene expression methods. Global gene expression methods can be used advantageously to measure a large population of system components including essentially all of the expressed genes of an organism or cell. Examples of methods well known in the art applicable to measuring a change in expression of a population of genes include cDNA sequencing, clone hybridization, differential display, subtractive hybridization, cDNA fragment fingerprinting serial analysis of gene expression (SAGE), and DNA microarrays. These methods are useful, for example, for identifying differences in gene expression under different conditions of a biochemical system. Methods of detecting changes in gene expression can be performed both qualitatively or quantitatively.

As disclosed herein, a useful method of monitoring gene expression is hybridization of sample mRNA to a DNA microarray. A DNA microarray is a useful tool for study of a biochemical system because the sequences of specific oligonucleotides or cDNAs that represent each system component are generally located at specific physical sites on the microarray. In addition, the relative concentration of a given transcript in two different samples can be readily determined. A variety of methods can be used for labeling samples for measurements of gene expression using a DNA microarray method. For example, mRNA can be labeled directly, such as by using a psoralen-biotin derivative or by ligation to an RNA molecule carrying biotin, or labeled nucleotides can be incorporated into cDNA during or after reverse transcription of polyadenylated RNA, or cDNA having a T7 promoter at the 5' end can be generated and used as a template for a reverse transcription reaction in which labeled nucleotides are incorporated into cDNA. Commonly used labels include the fluorophores fluorescein, Cy3, and Cy5, and non-fluorescent biotin, which can be subsequently labeled by staining with a fluorescent streptavidin conjugate. The use of Cy3 and Cy5 is shown in Example II, which describes a two-color hybridization strategy commonly used with DNA microarrays.

A variety of methods well known in the art can be used to monitor protein levels either directly or indirectly. Such methods include western blotting, two-dimensional gels, methods based on protein or peptide chromatographic separation, methods that use protein-fusion reporter constructs and colorimetric readouts, methods based on characterization of actively translated polysomal mRNA, and mass spectrometric detection. Additionally, aptamers can be used to detect specific polypeptides in a sample. Aptamers are oligonucleotides having binding affinity for polypeptides (Tuerk and Gold, *Science* 249:505-510 (1990); Ellington and Szostak, *Nature* 346:818-822 (1990); Joyce, *Curr. Opin. Struct. Biol.* 4:331-336 (1994); Gold et al., *Annu. Rev. Biochem.* 64:763-797 (1995); Jayasena, *Clin. Chem.* 45:1628-1650 (1999); Famulok and Mayer, *Curr. Top. Microbiol. Immunol.* 243:123-136 (1999)). A diversity of at least 1015 species can be synthesized. For example, DNA apatmers can be synthesized with variable nucleic acid sequences flanked on each end by recognition sites for PCR primers. If desired, apatamers that bind to a polypeptide can be selected and amplified, and such apatmers can have affinities greater than antibodies.

One convenient method for determining expression levels of molecules is to use a direct quantitation method such as the isotope-coded affinity tag (ICAT) method (Gygi et al., *Nature Biotechnol.* 17:994-999 (1999)). The ICAT method involved the comparison of a test sample and reference sample which are differentially labeled with isotopes that can be distinguished using mass spectrometry, as described in more detail below. In addition to using an ICAT reagent that modifies polypeptides or fragments thereof having particular amino acids, polypeptide profiles, for example, a peptide map of a polypeptide where the peptides can be correlated with the polypeptide. Use of a peptide map to correlate with a polypeptide expression level can be used to obviate the labeling required for using the ICAT method, if desired.

In determining a change in expression of a component, it can be advantageous to measure both mRNA and polypeptide levels of the component because a difference in an mRNA expression level in response to a perturbation may not correspond to the difference in polypeptide expression level due to post-translational modifications. Measurement of both mRNA and polypeptide expression levels is useful for identifying perturbation-induced changes in component expression that are not detectable using either mRNA or polypeptide expression measurement alone. However, it is not necessary that component expression levels be monitored by measuring both mRNA and polypeptide expression levels. Correlative changes between other characteristics of components of a biochemical system can also reveal changes in component behaviors that are not detectable using another method.

A change in expression of a component can be measured using a variety of methods. Components that are homologous generally have segments of high sequence identity in mRNA and polypeptide sequence. Components sharing a high degree of similarity can be indistinguishable by certain methods of mRNA or polypeptide analysis. Homologous genes that cannot be distinguished based on mRNA expression profiles can be distinguished at the protein level using a method such as the ICAT technique. A variety of methods known in the art can be applied to determining a change in expression of components that are homologous to each other. Such methods include the methods described herein and other well-known techniques such as, for example, oligonucleotide assays and two dimensional protein gels. These methods can similarly be applied if the change in expression of a component which is expressed at particularly low or high levels cannot be measured accurately by a particular technique due to low signal-to-noise ratio or saturation of the detection method. Thus, a change in expression or activity of a component can be determined using a variety of techniques, either independently of each other, or in combination.

The methods of the invention involve the measurement of a change in expression of a system component. A direct quantitation method useful for determining the level of expression of a molecule in a sample is the isotope-coded affinity tag (ICAT) method (Gygi et al., *Nature Biotechnol.* 17:994-999 (1999) which is incorporated herein by reference). The ICAT method uses an affinity tag that can be differentially labeled with an isotope that is readily distinguished using mass spectrometry, for example, hydrogen and deuterium. The ICAT affinity reagent consists of three elements, an affinity tag, a linker and a reactive group.

One element of the ICAT affinity reagent is an affinity tag that allows isolation of peptides coupled to the affinity reagent by binding to a cognate binding partner of the affinity tag. A particularly useful affinity tag is biotin, which binds with high affinity to its cognate binding partner avidin, or related molecules such as streptavidin, and is therefore stable to further biochemical manipulations. Any affinity tag can be used so long as it provides sufficient binding affinity to its cognate binding partner to allow isolation of peptides coupled to the ICAT affinity reagent.

A second element of the ICAT affinity reagent is a linker that can incorporate a stable isotope. The linker has a sufficient length to allow the reactive group to bind to a sample polypeptide and the affinity tag to bind to its cognate binding partner. The linker also has an appropriate composition to allow incorporation of a stable isotope at one or more atoms. A particularly useful stable isotope pair is hydrogen and deuterium, which can be readily distinguished using mass spectrometry as light and heavy forms, respectively. Any of a number of isotopic atoms can be incorporated into the linker so long as the heavy and light forms can be distinguished using mass spectrometry. Exemplary linkers include the 4,7,10-Trixie-1,13-tridecanediamine based linker and its related deuterated form, 2,2',3,3',11,11',12,12'-octadeutero-4,7,10-Trixie-1,13-tridecanediamine, described by Gygi et al. (supra, 1999). One skilled in the art can readily determine any of a number of appropriate linkers useful in an ICAT affinity reagent that satisfy the above-described criteria.

The third element of the ICAT affinity reagent is a reactive group, which can be covalently coupled to a polypeptide in a sample. Any of a variety of reactive groups can be incorporated into an ICAT affinity reagent so long as the reactive group can be covalently coupled to a sample molecule. For example, a polypeptide can be coupled to the ICAT affinity reagent via a sulfhydryl reactive group, which can react with free sulfhydryls of cysteine or reduced cystines in a polypeptide. An exemplary sulfhydryl reactive group includes an iodoacetamido group, as described in Gygi et al., supra (1999). Other exemplary sulfhydryl reactive groups include maleimides, alkyl and aryl halides, -haloacyls and pyridyl disulfides. If desired, the sample polypeptides can be reduced prior to reacting with an ICAT affinity reagent, which is particularly useful when the ICAT affinity reagent contains a sulfhydryl reactive group.

A reactive group can also react with amines such as Lys, for example, imidoesters and N-hydroxysuccinimidyl esters. A reactive group can also react with carboxyl groups found in Asp or Glu, or the reactive group can react with other amino acids such as His, Tyr, Arg, and Met. Methods for modifying side chain amino acids in polypeptides are well known to those skilled in the art (see, for example, Glazer et al., "Laboratory Techniques in Biochemistry and Molecular Biology: Chemical Modification of Proteins," Chapter 3, pp. 68-120, Elsevier Biomedical Press, New York (1975); Pierce Catalog (1994), Pierce, Rockford Ill.). One skilled in the art can readily determine conditions for modifying sample molecules by using various reagents, incubation conditions and time of incubation to obtain conditions optimal for modification of sample molecule for use in methods of the invention.

The ICAT method is based on derivatizing a sample molecule such as a polypeptide with an ICAT affinity reagent. A control reference sample and a sample from an individual to be tested are differentially labeled with the light and heavy forms of the ICAT affinity reagent. The derivatized samples are combined and the derivatized molecules cleaved to generate fragments. For example, a polypeptide molecule can be enzymatically cleaved with one or more proteases into peptide fragments. Exemplary proteases useful for cleaving polypeptides include trypsin, chymotrypsin, pepsin, papain, Staphylococcus aureus (V8) protease, and the like. Polypeptides can also be cleaved chemically, for example, using CNBr or other chemical reagents.

Once cleaved into fragments, the tagged fragments derivatized with the ICAT affinity reagent are isolated via the affinity tag, for example, biotinylated fragments can be isolated by binding to avidin in a solid phase or chromatographic format. If desired, the isolated, tagged fragments can be further fractionated using one or more alternative separation techniques, including ion exchange, reverse phase, size exclusion affinity chromatography and the like. For example, the isolated, tagged fragments can be fractionated by high performance liquid chromatography (HPLC), including microcapillary HPLC.

The fragments are analyzed using mass spectrometry (MS). Because the sample molecules are differentially labeled with light and heavy affinity tags, the peptide fragments can be distinguished on MS, allowing a side-by-side comparison of the relative amounts of each peptide fragment from the control reference and test samples. If desired, MS can also be used to sequence the corresponding labeled peptides, allowing identification of molecules corresponding to the tagged peptide fragments.

An advantage of the ICAT method is that the pair of peptides tagged with light and heavy ICAT reagents are chemically identical and therefore serve as mutual internal standards for accurate quantification (Gygi et al., supra, 1999). Using MS, the ratios between the intensities of the lower and upper mass components of pairs of heavy- and light-tagged fragments provides an accurate measure of the relative abundance of the peptide fragments. Furthermore, a short sequence of contiguous amino acids, for example, 5-25 residues, contains sufficient information to identify the unique polypeptide from which the peptide fragment was derived (Gygi et al., supra, 1999). Thus, the ICAT method can be conveniently used to identify differentially expressed molecules, if desired.

The above-described ICAT method can be performed as tandem MS/MS. A dual mode of MS can be performed in which MS alternates in successive scans between measuring relative quantities of peptides and recording of sequence information of selected peptides (Gygi et al., supra, 1999). Other modes of MS include matrix-assisted laser desorption-time of flight (MALDI-TOF), an electrospray process with MS, and ion trap. In ion trap MS, fragments are ionized by electrospray and then put into an ion trap. Trapped ions can then be separately analyzed by MS upon selective release from the ion trap. Fragments can also be generated in the ion trap and analyzed.

In addition to polypeptides, the ICAT method can similarly be applied to determining the expression level of nucleic acid molecules. In such a case, the ICAT affinity reagent incorporates a reactive group for a nucleotide, for example, a group reactive with an amino group. The ICAT affinity reagent can incorporate functional groups specific for a particular nucleotide or a nucleotide sequence of 2 or more nucleotides. The nucleic acid molecules can be cleaved enzymatically, for example, using one or more restriction enzymes, or chemically (see Sambrook et al., supra, 1989; Ausubel et al., supra, 1999).

The methods of the invention for detecting nucleic acids and/or polypeptides, particularly methods useful for detecting large numbers of molecules such as microarray-based methods, can be combined with well known methods of detecting expression levels of small molecules to determine the expression levels of more than one type of molecule. For example, methods of analyzing small molecules such as glucose, sugars, carbohydrates, calcium, amino acids, lipids, neurotransmitters, as well as other small molecules disclosed herein, can be analyzed using well known clinical chemistry methods (see, for example, Tietz Textbook of Clinical Chemistry, 3rd edition, Burtis and Ashwood, eds., W. B Saunders Company, Philadelphia (1999)). Exemplary methods of determining the levels of small molecules include the use of enzyme-based assays, including colorimetric and radioenzymatic (incorporation of radioactive substrates), chromogenic assays, spectrophotometry, fluorescence spectroscopy, liquid chromatography, including ion exchange, affinity, HPLC, paper chromatography, gas chromatography, photometry atomic absorption spectrometry, emission spectroscopy, including inductively coupled plasma emission spectroscopy, mass spectrometry, inductively coupled mass spectrometry, neutron activation analysis, X-ray fluorescence spectrometry, electrochemical techniques such as anodic stripping voltametry, polarographic techniques, flame emission spectrophotometry, electrochemical methods such as ion selective electrodes, chemical titration, and the like (Tietz Textbook of Clinical Chemistry, second edition, Burtis and Ashwood, eds., W. B. Saunders Company, Philadelphia (1994); Tietz Textbook of Clinical Chemistry, 3rd ed., Burtis and Ashwood, eds., W. B. Saunders Co., Philadelphia (1999)). Small molecule assay methods can also be adapted to accommodate multiple samples, including solid phase microarray-based formats.

A change in expression or activity of a population of components can be monitored using a variety of global gene expression analysis methods, such as DNA and protein microarrays, and large throughput formatted immunological detection methods, such as ELISA and RIA. The use of global analysis methods can result in identifying a large number of candidate network components. To identify common patterns of expression among genes, and to reduce the number of distinct expression profiles under consideration, a set of significantly-effected genes can be divided into clusters using manual examination of the data or by using statistical methods. Statistical methods useful for clustering having similar expression ratios over all perturbations include, for example, self-organizing maps, K-tuple means clustering and hierarchical clustering. Genes that have similar patterns of expression in a series of perturbations can be functionally related.

The methods of the invention involve measuring the expression or activity of a component in a sample containing a biochemical system. Such a sample can be isolated from a variety of sources. For example, a sample can be prepared from any biological fluid, cell, tissue, organ or portion thereof, or species. A sample can be obtained or derived from the individual. For example, a sample containing a biochemical system can be a histologic section of a specimen obtained by biopsy, or cells that are placed in or adapted to tissue culture. A sample containing a biochemical system further can be a subcellular fraction or extract, such as, for example, a nuclear or cytoplasmic cellular fraction. A sample can also be a isolated preparation of nucleic acid or polypeptide. A sample can be prepared by methods known in the art suitable for the particular methods used for measuring the expression or activity of a component, such as the methods described herein. Those skilled in the art will know how to prepare a sample for use with the selected analytical methods for measuring nucleic acids, polypeptides, and other biological molecules.

The methods of the invention can be applied to small samples such as cells removed from a particular tissue or tumor. Methods well known in the art for amplification of mRNA, such as, for example, PCR-based amplification and template-directed in vitro transcription(IVT) can be used for generating a sample to be used in the methods of the invention. Methods of amplifying nucleic acids by reverse transcription are well known to those skilled in the art (see, for example, Dieffenbach and Dveksler, PCR Primer: A Laboratory Manual, Cold Spring Harbor Press (1995)).

A biochemical system can be contained within a specimen obtained from an individual representative of a reference or pathological biochemical system. To determine the expression level of a component in complex biochemical system, such as an animal, a specimen is obtained from the animal that is representative of the expression level of molecules in the animal. A specimen can be obtained from an animal as a fluid or tissue specimen. For example, a tissue specimen can be obtained as a biopsy such as a skin biopsy, tissue biopsy or tumor biopsy. A fluid specimen can be blood, urine, saliva or other bodily fluids. A fluid specimen is particularly useful in methods of the invention since fluid specimens are readily obtained from an individual. Methods for collection of specimens are well known to those skilled in the art (see, for example, Young and Bermes, in Tietz Textbook of Clinical Chemistry, 3rd ed., Burtis and Ashwood, eds., W. B. Saunders, Philadelphia, Chapter 2, pp. 42-72 (1999)). A specimen can optionally be fractionated into cell populations or subpopulations. A particularly useful method of fractionating a population of cells is to use ligands that bind to a cell surface molecule, for example, antibodies that bind to a cell surface antigen.

If desired, multiple specimens from a mammal can be combined and analyzed as a single specimen representative of a data element, such as expression level, of molecules in the mammal. Alternatively, multiple specimens from a mammal can be separately used to determine data elements, such as expression levels, of molecules in the different specimens, and then the data elements, such as expression levels, from multiple specimens compared or averaged, so long as the specimens from the reference population are treated in the same manner or the expression levels are correlated with appropriate controls and/or validation methods, as disclosed herein.

A specimen useful in methods of the invention contains one or more molecules that are representative of the gene expression level and/or cellular expression level of components in the mammal. Methods for obtaining specimens that preserve the expression profile of molecules in a specimen, including nucleic acids such as mRNA, polypeptides, small molecules, or post-translational modifications of such molecules, are well known to those skilled in the art. Such methods include the use of appropriate buffers and/or inhibitors, including nuclease, protease and phosphatase inhibitors, that preserve or minimize changes in the expression level of molecules in the specimen. Such inhibitors include, for example, chelators such as ethylenediamne tetraacetic acid (EDTA), ethylene glycol bis($\beta$-aminoethyl ether)-N,N,N',N'-tetraacetic acid (EGTA), protease inhibitors such as phenylmethylsulfonyl fluoride (PMSF), aprotinin, leupeptin, antipain and the like, and phosphatase inhibitors such as phosphate, sodium fluoride, vanadate and the like. Appropriate buffers and conditions for isolating molecules are well known to those skilled in the art and can be varied depending, for example, on the type of molecule in the specimen to be characterized with respect to expression level (see, for example, Ausubel et al., Current Protocols in Molecular Biology (Supplement 47), John Wiley & Sons, New York (1999); Harlow and Lane, Antibodies: A Laboratory Manual (Cold Spring Harbor Laboratory Press (1988); Harlow and Lane, Using Antibodies: A Laboratory Manual, Cold Spring Harbor Press (1999); Tietz Textbook of Clinical Chemistry, 3rd ed., Burtis and Ashwood, eds., W. B. Saunders, Philadelphia, (1999)).

If desired, the specimen can be incubated or processed in a manner to increase the availability of molecules in the specimen for analytical methods disclosed herein. For example, if the molecule to be detected in the specimen is a nucleic acid and the detection method involves binding to another nucleic acid, the specimen can be incubated in buffers and under conditions useful for preserving nucleic acids, particularly mRNA, and for detecting hybridization between nucleic acid molecules. Such conditions are well known to those skilled in the art (Sambrook et al., Molecular Cloning: A Laboratory Manual, 2nd ed., Cold Spring Harbor Press, Plainview, New York (1989); Ausubel et al., Current Protocols in Molecular Biology (Supplement 47), John Wiley & Sons, New York (1999)). Furthermore, a specimen containing mRNA can be converted to cDNA, if desired, using reverse transcriptase.

A specimen can also be processed to eliminate or minimize the presence of interfering substances. For example, a specimen containing nucleic acids can be fractionated or extracted to remove potentially interfering non-nucleic acid molecules. The specimen can also be treated to decrease interfering nucleic acids, for example, by treating a specimen with DNase or RNase to increase the ability to detect RNA or DNA, respectively. Various methods to fractionate a fluid specimen or cell extract are well known to those skilled in the art, including subcellular fractionation or chromatographic techniques such as ion exchange, hydrophobic and reverse phase, size exclusion, affinity, hydrophobic charge-induction chromatography, and the like (Ausubel et al., supra, 1999; Scopes, Protein Purification: Principles and Practice, third edition, Springer-Verlag, New York (1993); Burton and Harding, J. Chromatogr. A 814:71-81 (1998)).

If the molecule to be detected in the specimen is a polypeptide and the detection method involves binding the polypeptide to an antibody, the specimen can be incubated in buffers suitable for immunological detection methods, for example, the addition of detergents, including denaturants such as sodium dodecyl sulfate (SDS), if desired (Harlow and Lane, supra, 1988; Harlow and Lane, supra, 1999). The specimen can also be fractionated, for example, into cellular or subcellular fractions, if desired.

Bodily fluid specimens are particularly useful in methods of the invention due to ready availability. A particularly useful fluid specimen is a blood specimen, particularly one containing leukocytes (WBCs). A specimen from a mammal containing leukocytes is representative of the physiological state of the mammal and, therefore, is useful in determining data elements of components, such as expression levels of components, in a mammal that are indicative of a reference or perturbed state. Gene and cellular expression in leukocytes reflects many physiological systems and states in the cell, for example, nervous, immune, cardiovascular, gastrointestinal, endocrine, hepatic, lymphatic, neuromuscular, renal, respiratory, skeletal, and urogenital systems. Perturbations in organs of these systems are reflected in the leukocytes. Therefore, using an analytical method that is useful for detecting molecules in a leukocyte specimen from a mammal is particularly useful in methods of the invention.

When using leukocytes as a specimen, a serum specimen from a mammal containing leukocytes can be fractionated to isolate leukocytes, if desired, or subfractionated, for example, into macrophages, T cells, B cells, granuolocytes, monocytes, neutrophils, eosinophils, basophils, mast cells, and the like. Serum can be fractionated into a leukocyte fraction or subfractionated using methods well known in clinical chemistry and blood analysis. Luekocytes or subfractions thereof can also be isolated by affinity binding methods specific for leukocytes or leukocyte subfractions. For example, an antibody binding step using a leukocyte-specific antibody can be used to isolate leukocytes. The leukocytes can optionally be eluted from the affinity matrix, or the bound leukocytes can be directly used by lysing the leukocytes bound to the affinity matrix. Similarly, antibodies specific for leukocyte subfractions such as T cell or B cell specific antibodies can be used to subfractionate leukocytes. In addition, antibodies specific to cell surface markers such as CD markers can be used to identify and/or isolate a subpopulation of cells. Such cell surface markers can also be used to determine the ratios of particular cell types in a specimen, for example, using a cell sorting apparatus, which can also be an indication of a perturbation state of a cell.

The methods of the invention can be performed using semi-automated or automated formats. Those skilled in the art will know how to automate steps of sample preparation and data analysis, including automated generation and updating of representations of multidimensional shape spaces and integrated multidimensional data spaces. Multidimensional shape spaces and integrated multidimensional data spaces can be presented in the form of a web-based tool for analysis and discovery of biochemical system and system component function, and can serve as reference multidimensional shape spaces and integrated multidimensional data spaces useful for web-wide comparative studies.

The compounds of the invention for restoring a biochemical system to a reference state can be used to restore a reference state of a biochemical system or constituent system of an individual having a pathological condition characterized by a perturbation state of a biochemical system. The method consists of administering an effective amount of one or more compounds that restore a biochemical system to a reference state in an individual having a perturbation state of a biochemical system.

A multidimensional shape space or integrated multidimensional data space prepared from a specimen obtained from an individual having a pathological condition can be compared to a reference multidimensional shape space or integrated multidimensional data space, such as that from a normal or non-diseased specimen. The methods of the invention for restoring a biochemical system to a reference state involve administering an effective amount of a compound that restores a biochemical system to a reference state. Such a compound can be identified using methods known in the art or the methods described above, for example.

For treating or reducing the severity of a pathological condition a compound that a biochemical system to a reference state can be formulated and administered in a manner and in an amount appropriate for the condition to be treated; the weight, gender, age and health of the individual; the biochemical nature, bioactivity, bioavailability and side effects of the particular compound; and in a manner compatible with concurrent treatment regimens. An appropriate amount and formulation for a particular therapeutic application in humans can be extrapolated based on the activity of the compound in recognized animal models of the particular disorder.

The total amount of a compound that restores a biochemical system to a reference state can be administered as a single dose or by infusion over a relatively short period of time, or can be administered in multiple doses administered over a more prolonged period of time. Additionally, a compound can be administered in a slow-release matrix, which can be implanted for systemic delivery at or near the site of the target tissue.

A compound that restores a biochemical system to a reference state can be administered to an individual using a variety of methods known in the art including, for example, intravenously, intramuscularly, subcutaneously, intraorbitally, intracapsularly, intraperitoneally, intracisternally, intra-articularly, intracerebrally, orally, intravaginally, rectally, topically, intranasally, or transdermally.

A compound that restores a biochemical system can be administered to a subject as a pharmaceutical composition comprising the compound and a pharmaceutically acceptable carrier. The choice of pharmaceutically acceptable carrier depends on the route of administration of the compound and on its particular physical and chemical characteristics. Pharmaceutically acceptable carriers are well known in the art and include sterile aqueous solvents such as physiologically buffered saline, and other solvents or vehicles such as glycols, glycerol, oils such as olive oil and injectable organic esters. A pharmaceutically acceptable carrier can further contain physiologically acceptable compounds that stabilize the compound, increase its solubility, or increase its absorption. Such physiologically acceptable compounds include carbohydrates such as glucose, sucrose or dextrans; antioxidants, such as ascorbic acid or glutathione; chelating agents; and low molecular weight proteins.

In addition, a formulation of a compound that restores a biochemical system to a reference state can be incorporated into biodegradable polymers allowing for sustained release of the compound, the polymers being implanted in the vicinity of where drug delivery is desired, for example, at the site of a tumor or implanted so that the compound is released systemically over time. Osmotic minipumps also can be used to provide controlled delivery of specific concentrations of a compound through cannulae to the site of interest, such as directly into a tumor growth or other site of a pathology involving a perturbation state. The biodegradable polymers and their use are described, for example, in detail in Brem et al., *J. Neurosurg.* 74:441-446 (1991).

It is understood that modifications which do not substantially affect the activity of the various embodiments of this invention are also provided within the definition of the invention provided herein. Accordingly, the following examples are intended to illustrate but not limit the present invention.

EXAMPLE I

Logistic Regression Analysis

This example describes the analysis of a data set for three biochemical system states and two component expression levels using logistic regression analysis. The two component expression levels are represented by a multidimensional coordinate point.

Figure 3A:
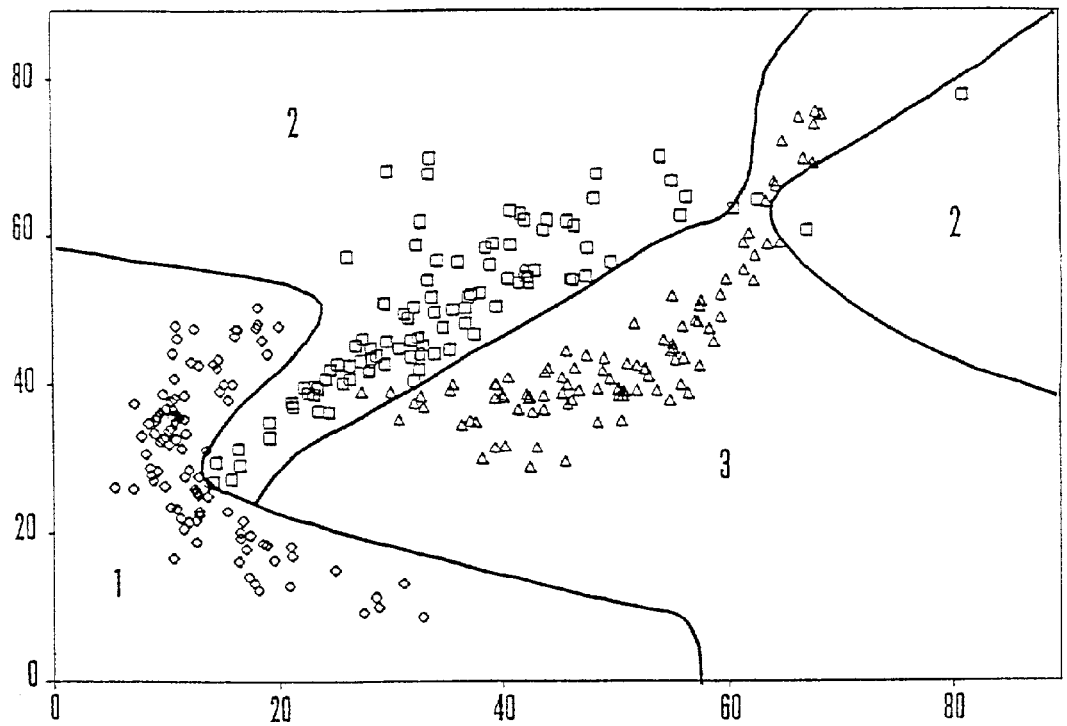
FIGS. 3A and B shows a data set for three networks under three states of a biochemical system and two component data element levels determined by logistic regression analysis, with FIG. 3B showing the coordinates of networks in biochemical systems "A" (x) and "B" (+).

The data set was created starting with pseudorandom computer-generated numbers and then applying a different mathematical transformation for each biochemical system reference group, each reference group representing a different state of the biochemical system. For the data set shown in FIG. 3A for three states of a biochemical system and two molecular expression levels, the resulting classification regions are shown using logistic regression analysis under the assumptions that the costs of misclassification are all equal, and the prior probabilities are 0.2, 0.5, and 0.3 for the three groups. Because biochemical system state 2 is the most common in the population, the classification tends to favor this group at the upper right where data are sparse.

The classification regions are based on three separate logistic regression analyses, one to predict each biochemical system state, where each analysis used the molecular expression levels of components for all biochemical system states but coded the independent variable to indicate the biochemical system state to be predicted. To allow for the curvature in the data, the predictor variables were chosen to be cubic polynomials in the predictor variables with a backward stepwise selection process to omit terms that do not contribute to the prediction. The resulting predicted probability for each biochemical system state can be scaled by its prior probability of occurrence in the population, and the resulting scores compared. The biochemical system state with the largest score is the chosen classification, while the relative values of all three scores indicate the relative likelihoods of the three biochemical system states.

The assignment of new biochemical systems, which can be individuals, "A" and "B" to one of the three defined biochemical system states were determined. The molecular expression levels of two new biochemical systems, or individuals "A" and "B", with unknown biochemical states, are shown in FIG. 4B, with A indicated as "x" and B indicated as "+."

The following method was used for computing the degree of confidence in the assignment of a new individual: (a) compute the predicted probability for each biochemical system state using the results of the logistic regression analyses (where these results do not include the new individual) evaluated at the expression levels for the new individual; (b) multiply each of these numbers by the prior probability of that biochemical system state occurring in the population; (c) divide each of the three resulting numbers by their sum in order to convert them into probabilities that add up to 1. The results of these steps are the relative probabilities that the new individual belongs to each biochemical system state group.

Figure 3B:
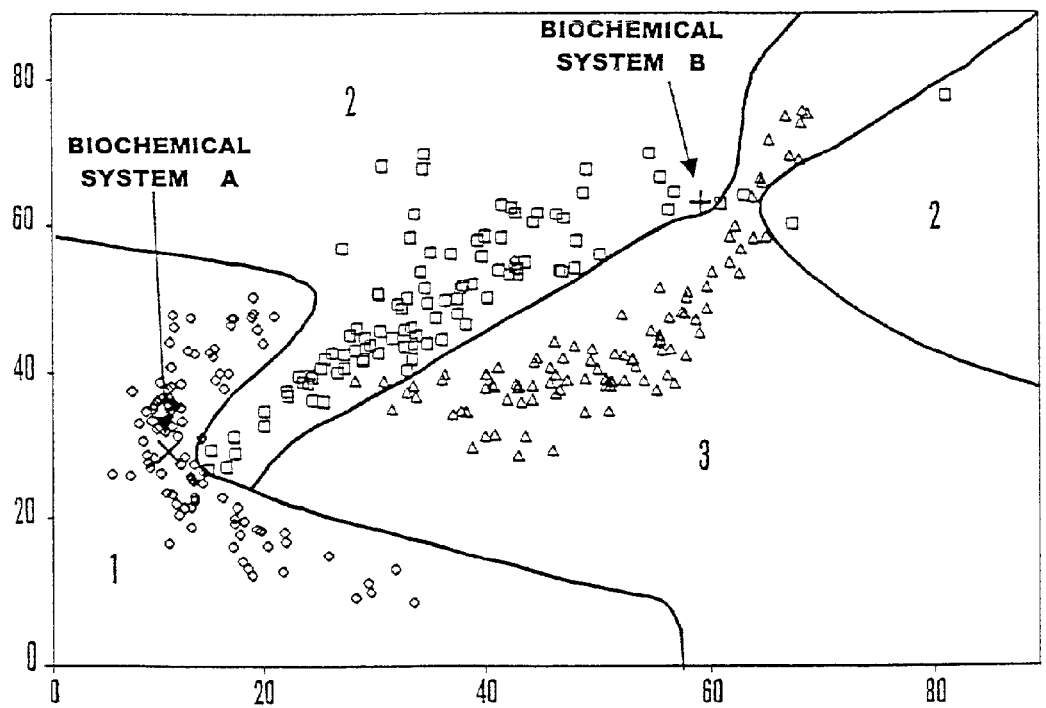

The degree of confidence in the assignment of individual A to biochemical system group 1 was assessed by examining the relative probabilities of individual A belonging to each biochemical system state group, and the results were consistent with FIG. 3B, which shows that individual A is clearly well-described as being within the data for individuals with biochemical system state 1. The results show that individual A has a 97.0% chance of being in biochemical system state 1, a 2.8% chance of being in biochemical system state 2, and a 0.2% chance of being in biochemical system state 3, as predicted using the model.

Individual B was also assigned to a biochemical system state, although the degree of confidence was less than for individual A. The degree of confidence in the assignment of individual B to biochemical system group 2 was assessed, and the results are consistent with FIG. 3B, which shows that individual B is near the boundary that separates individuals with biochemical system state 2 from those having biochemical system state 3. The results show that individual B has a 2.1% chance of being in biochemical system state 1, a 74.2% chance of being in biochemical system state 2, and a 23.6% chance of being in biochemical system state 3, as predicted using the model.

This example shows that logistic regression analysis can be used classify the biochemical system states of a group of reference individuals and the assignment of an individual to a reference biochemical system state.

Although the invention has been described with reference to the disclosed examples, it should be understood that various modifications can be made without departing from the spirit of the invention.

What is claimed is:

1. A method for assigning a cellular function to a component of a biochemical system, comprising:
    (a) physically perturbing a component of a network in a biochemical system;
    (b) measuring a data element for each of n components of said perturbed biochemical system, wherein n is three or more;
    (c) determining a multidimensional coordinate point in n-dimensional space representative of said data elements for each of said three or more measured components of said perturbed biochemical system, said multidimensional coordinate point comprising values for said data elements for each of said n measured components, wherein n corresponds to the number of measured biochemical components within said perturbed biochemical system;
    (d) comparing said multidimensional coordinate point to a reference data element region;
    (e) determining if said multidimensional coordinate point is within or outside said reference data element region, and
    (f) providing an output to a user of said determination in step (e), wherein a multidimensional coordinate point outside of said reference data element region indicates that said component is linked to said perturbed biochemical network, and is thereby assigned a cellular function of said network.

2. The method of claim 1, wherein said data element is a data element selected from the group consisting of nucleic acid expression element and polypeptide expression element.

3. A method for assigning a cellular function to a component of a biochemical system, comprising:
    (a) measuring a data element for each of n components of a physically perturbed biochemical system, wherein n is three or more;
    (b) determining a multidimensional coordinate point in n-dimensional space representative of data elements for each of said three or more measured components in a biochemical network of said physically perturbed biochemical system, said multidimensional coordinate point comprising values for said data elements for each of said n measured components, wherein n corresponds to the number of measured biochemical components within said perturbed biochemical system;

(c) comparing said multidimensional coordinate point to a network-associated reference expression region of said set of components;

(d) determining if said multidimensional coordinate point is outside of said network-associated reference expression region, and (e) providing an output to a user of said determination in step (d), wherein a multidimensional coordinate point outside of said network-associated reference expression region indicates a perturbed state of said network, said component being linked to said perturbed network and thereby being assigned a cellular function of said network.

4. The method of claim 3, wherein said biochemical system is selected from the group consisting of a cell, tissue, organism and subcellular system.

5. The method of claim 3, wherein said data element is an expression data element.

6. The method of claim 3, wherein said reference expression region indicates a normal state of a biochemical system.

7. The method of claim 3, wherein said components of the biochemical network comprise nucleic acids.

8. The method of claim 3, wherein said components of the biochemical network comprise polypeptides.

9. A method for assigning a cellular function to a component of a biochemical system, comprising:
(a) measuring a data element for each of n components of a physically perturbed biochemical system, wherein n is three or more;

(b) determining a multidimensional coordinate point in n-dimensional space representative of data elements of said three or more measured components in a biochemical pathway of said physically perturbed biochemical system, said multidimensional coordinate point comprising values for said data elements for each of said n measured components, wherein n corresponds to the number of measured biochemical components within said perturbed biochemical system;

(c) comparing said multidimensional coordinate point to a pathway-associated reference expression region of said set of components;

(d) determining if said multidimensional coordinate point is outside of said pathway-associated reference expression region, and (e) providing an output to a user of said determination in step (d), wherein a multidimensional coordinate point outside of said pathway-associated reference expression region indicates a perturbed state of said pathway, said component being linked to said perturbed pathway and thereby being assigned a cellular function of said pathway.

10. The method of claim 9, wherein said biochemical system is selected from the group consisting of a cell, tissue, organism and subcellular system.

11. The method of claim 9, wherein said data element is an expression data element.

12. The method of claim 9, wherein said reference expression region indicates a normal state of a biochemical system.

13. The method of claim 9, wherein said components of the biochemical network comprise nucleic acids.

14. The method of claim 9, wherein said components of the biochemical network comprise polypeptides.

* * * * *